(12) United States Patent
Karoum et al.

(10) Patent No.: US 10,656,134 B2
(45) Date of Patent: May 19, 2020

(54) ISOTHERMAL ANALYSIS SYSTEM AND METHOD TO DETERMINE AT LEAST ONE TYPE OF CARBON COMPOUNDS IN DRILL CUTTINGS

(71) Applicant: GEOSERVICES EQUIPEMENTS, Roissy-en-France (FR)

(72) Inventors: Reda Karoum, Houston, TX (US); Karim Bondabou, Roissy-en-France (FR); Pawel Kasprzykowski, Roissy-en-France (FR); Jerome Breviere, Roissy-en-France (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 79 days.

(21) Appl. No.: 15/100,081

(22) PCT Filed: Dec. 2, 2014

(86) PCT No.: PCT/US2014/068050
§ 371 (c)(1),
(2) Date: May 27, 2016

(87) PCT Pub. No.: WO2015/084784
PCT Pub. Date: Jun. 11, 2015

(65) Prior Publication Data
US 2017/0045491 A1   Feb. 16, 2017

Related U.S. Application Data

(60) Provisional application No. 61/910,430, filed on Dec. 2, 2013.

(30) Foreign Application Priority Data

Dec. 2, 2013   (EP) .................................. 13306648

(51) Int. Cl.
*G01N 33/24* (2006.01)
*G01N 31/12* (2006.01)
*G01N 1/28* (2006.01)

(52) U.S. Cl.
CPC ........... *G01N 33/241* (2013.01); *G01N 1/286* (2013.01); *G01N 31/12* (2013.01)

(58) Field of Classification Search
CPC ............................... G01N 33/24; G01N 31/12
(Continued)

(56) References Cited

U.S. PATENT DOCUMENTS 2,768,793 A * 10/1956 Bonner ..................... B02C 1/14
241/199.9
3,711,765 A * 1/1973 Overton ................ E21B 49/005
324/348

(Continued)

FOREIGN PATENT DOCUMENTS

WO   2012030425 A1   3/2012

OTHER PUBLICATIONS

Brill, T. B. et al, Applied Spectroscopy 1992, 46, 900-911.*
(Continued)

*Primary Examiner* — Arlen Soderquist

(57) ABSTRACT

A computer system including a processor executing processor-executable code stored in a non-transitory processor-readable medium, causing the processor to receive a signal via an input port, including data indicative of an amount of a combustion product produced by a sample of drill cuttings subjected to oxidation at a constant temperature (1000° C. or 650° C. 100° C.) as a function of time and process the data according to a predetermined logic to: locate a peak in the amount of the combustion product produced at a set of instants in time; correlate the set of instants in time with the presence in the sample of an organic carbon from a con- (Continued)

taminant or light volatile carbon molecules, organic carbon, and inorganic carbon; calculate at least one of an amount of contaminant, a total amount of organic carbon, and a total amount of inorganic carbon; and output a signal indicative of the calculated amount.

21 Claims, 10 Drawing Sheets

(58) Field of Classification Search
USPC ........... 422/78–80; 436/29, 31–32, 114–118, 436/122, 133–134, 139–143, 145, 155, 436/157, 160
See application file for complete search history.

(56) References Cited

U.S. PATENT DOCUMENTS

| | | | | |
|---|---|---|---|---|
| 3,847,546 | A * | 11/1974 | Paul | G01N 30/12 436/157 |
| 3,861,874 | A * | 1/1975 | Krc | G01N 25/08 422/80 |
| 3,953,171 | A * | 4/1976 | Espitalie | G01N 31/00 436/32 |
| 4,106,908 | A | 8/1978 | Leplat-Gryspeerdt | |
| 4,153,415 | A | 5/1979 | Espitalie et al. | |
| 4,213,763 | A * | 7/1980 | Madec | G01N 31/12 422/80 |
| 4,244,917 | A * | 1/1981 | Woods | G01N 31/12 422/80 |
| 4,282,183 | A * | 8/1981 | Bredeweg | G01N 31/12 422/547 |
| 4,325,907 | A * | 4/1982 | Dembicki, Jr. | G01N 30/00 422/54 |
| 4,344,917 | A * | 8/1982 | Schorno | G01N 30/12 422/78 |
| 4,352,673 | A * | 10/1982 | Espitalie | G01N 31/12 436/145 |
| 4,352,781 | A * | 10/1982 | O'Brien | G01N 31/12 422/643 |
| 4,601,882 | A * | 7/1986 | Benner | G01N 31/005 422/78 |
| 4,606,649 | A * | 8/1986 | Mikhail | G01N 25/4866 374/10 |
| 4,824,790 | A * | 4/1989 | Carangelo | G01N 5/04 422/80 |
| 4,845,040 | A * | 7/1989 | Moon | G01N 31/12 436/120 |
| 5,064,617 | A * | 11/1991 | O'Brien | G01N 31/12 356/312 |
| 5,178,837 | A * | 1/1993 | Crisp | G01N 31/12 422/157 |
| 5,204,270 | A * | 4/1993 | LaCount | G01N 21/3504 422/80 |
| 5,236,353 | A * | 8/1993 | Adani | G01N 31/12 422/78 |
| 5,389,550 | A * | 2/1995 | Ishida | G01N 33/241 110/203 |
| 5,567,388 | A | 10/1996 | Morita et al. | |
| 5,786,225 | A * | 7/1998 | Lafargue | G01N 7/16 422/54 |
| 5,811,308 | A * | 9/1998 | Espitalie | G01N 33/241 422/54 |
| 5,843,787 | A | 12/1998 | Trabelsi et al. | |
| 7,772,004 | B2 * | 8/2010 | Lorant | G01N 33/241 422/68.1 |
| 8,492,153 | B2 | 7/2013 | Jones et al. | |
| 8,729,903 | B2 | 5/2014 | Srnka et al. | |
| 8,796,035 | B2 * | 8/2014 | Espitalie | G01N 33/24 422/78 |
| 2008/0026471 | A1 * | 1/2008 | Lorant | G01N 33/241 436/32 |
| 2008/0229849 | A1 * | 9/2008 | Doebler | B01L 7/52 73/864.91 |
| 2010/0034702 | A1 | 2/2010 | Akechi et al. | |
| 2011/0263034 | A1 * | 10/2011 | Espitalie | G01N 33/24 436/122 |
| 2012/0095687 | A1 | 4/2012 | LeCompte | |
| 2013/0262069 | A1 | 10/2013 | Leonard | |

OTHER PUBLICATIONS

Williams, P. T. et al, Applied Energy 2000, 66, 113-133.*
Torrente, M. C. et al, Fuel 2001, 80, 327-334.*
Du, Z. et al, Energy & Fuels 1991, 5, 214-221.*
Abuluwefa, H. T. et al, Metalurgical and Materials Transactions A 1997, 28A 1633-1641.*
Liu, J. et al, Journal of Thermal Analysis and Calorimetry 1999, 58, 447-453.*
Shimada, S. et al, Thermochimica Acta 2004, 419, 143-148.*
Ambalae, A. et al, Energy & Fuels 2006, 20, 560-565.*
Haddadin, R. A. et al, Industrial & Engineering Chemistry Process Design and Development 1974, 13, 332-336.*
Elder J. P., Fuel, 1983, 62, 580-584.*
Pan, Z. et al, AIChE Journal 1985, 31, 721-728.*
Miknis, F. P. et al, Report 1985, 70 pages.*
Charlton, B. G. et al, Fuel 1987, 66, 384-387.*
Thakur, D. S. et al, Industrial & Engineering Chemistry Research 1987, 26, 1351-1356.*
Skala, D. et al, Thermochimica Acta vol. 1988, 134, 353-358.*
Killingley, J. S. et al, Fuel 1988, 67, 1349-1352.*
Warne, S. St. J., TrAC Trends in Analytical Chemistry 1991, 10, 195-199.*
Reina, J. et al, Thermochimica Acta 1998, 320, 161-167.*
Ptacek, P. et al, Thermochimica Acta 2010, 501, 24-29.*
Ozgur, E. et al, Oil Shale 2012, 29, 190-201.*
Meng, F. et al, Energy & Fuels 2013, 27, 2923-2932.*
D.M Jarvie et al., Assessment of the gas potential and yields from Shales: the Barnett Shale model, D.M Jarvie and al, Oklahoma Geological Survey Circular 110, p. 37-50, 2005.
K.F.M et al., Investigation of cretaceous and tertiary kerogens in sediment of the weddell sea, Proceedings of the Ocean Drilling Program, Scientific Results, College station, 13, 189-197, 1990.
E. Lafargue et al., Rock-Eval 6 application in hydrocarbon exploration, production and in soil contamination studies, IFP revue, vol. 53, p. 421-437, 1998.
Akinselinwa Akinlua et al., Source rock potential selected cretaceous shales, Orange Basin, South Africa, International Geology Review, vol. 53, issue 13, 2011 (15 pages).
I. Girard and al., A comparison of seven methods for analysis of carbon in soils, Geological Survey of Canada, 2001. (24 pages).
B.A Schumacher, Methods for the determination of total organic carbon (TOC) in soil and sediments, US Environmental Protection Agency, Ecological Risk Assessment Support Center, 2002. (25 pages).
International Preliminary Report on Patentabililty issued in the related PCT Application PCT/US2014/068050, dated Jun. 7, 2016 (9 pages).
Extended Search Report issued in the related EP Application 13306648.0, dated Mar. 21, 2014 (9 pages).
Empower Software Data Acquisition and Processing Theory Guide, 2002, Milford, USA (226 pages).
International search report and written opinion issued in related internationai application PCT/US2014/068050, dated Mar. 20, 2015 (14 pages).

* cited by examiner

ISOTHERMAL ANALYSIS SYSTEM AND METHOD TO DETERMINE AT LEAST ONE TYPE OF CARBON COMPOUNDS IN DRILL CUTTINGS

BACKGROUND

The measurement of the total organic carbon present in solids or liquids is a common parameter used in a variety of industries, such as semiconductor, pharmaceutical, food, and petrochemical. In the petrochemical industry, the total organic carbon of rock from an oil or natural gas reservoir is known as a parameter that is considered in evaluating the quality of the reservoir. This is especially true when evaluating the quality of an oil or gas reservoir located within a rock known as "shale." For example, the total organic carbon of the shale is used to assess organic richness, original hydrocarbon potential, thermal maturity, gas content, and gas yields. To discover new sources of oil or natural gas, operators are looking for shale with sufficient total organic carbon and other evidence that amounts of gas had been formed from that total organic carbon in order to evaluate the interest and the quality of the reservoir. The technique used routinely to evaluate the quality of the shale is a standard tool for hydrocarbon exploration known as the Rock-Eval technique.

In soils and sediments such as drill cuttings, two basic forms of carbon compounds may be present: total inorganic carbon (TIC) and total organic carbon (TOC). The TIC includes carbon compounds from the carbonates (e.g., calcite, dolomite, siderite) present in the rock and/or soil, whereas the TOC comes from any organic matter (OM) present in the rock and/or soil. The organic matter is defined as a variety of materials ranging from simple molecules of various types such as sugars, complex proteins, to fats, waxes, or complex hydrocarbons.

Many methods exist to determine the TOC, but currently the method that utilizes dry combustion of carbon compounds is the most widely used. Many instruments are available in the market allowing the measurement of the TOC such as TOC-meters provided by Shimadzu (SSM-5000A), Horiba (EMIA-V), LECO or the RockEval6. The principle of the measurement is to oxidize a weighed ground-up or powdered sample such as drill cuttings and/or soil by gradually heating up the sample, first to a lower temperature to oxidize any organic molecules from light volatile carbon compounds to kerogen present, and then to a higher temperature to decompose carbonate compounds present in the sample. The combustion reaction will produce mainly carbon dioxide ($CO_2$), carbon monoxide (CO), but also other compounds such water ($H_2O$), nitrogen oxide and nitrogen dioxide (NO and $NO_2$), and sulfide oxide ($SO_2$). A suitable detector (e.g., IR, TCD) may measure the $CO_2$ produced as a function of temperature, and the measured $CO_2$ is related to a percentage of carbon compounds in the sample.

Two common methods are applied to calculate the TOC: a method by difference (indirect) and a direct calculation. The method by difference includes determining the total carbon content (TC) and the total inorganic content (TIC), followed by the calculation of the difference to determine the TOC (TOC=TC−TIC). The direct calculation involves analyzing a sample that is already free of carbonates, in which case the determined TC is equal to the TOC.

It is well known to determine the TOC of drill cuttings. However, drill cuttings are frequently contaminated with hydrocarbons or other organic compounds (e.g., from drilling fluids) which could introduce errors into the reading of the TOC, typically an over-estimation, in both the direct and indirect TOC calculation methods. In particular, due to the nature and the composition of some drilling fluids (e.g., oil-based drilling mud or drilling mud additives), field drill cutting samples contain extra carbon compounds that do not belong to the original organic matter present in the drill cuttings. As drilling fluids are complex mixtures including many carbon-containing compounds, contaminates including drilling fluids are generally removed before analyzing drill cuttings for TOC such as via an appropriate thermal cleaning procedure (e.g., gradually heating the drill cuttings to a relatively low temperature to remove the contaminants) or via any chemical cleaning procedure (e.g., chemically removing the contaminants using an appropriate solvent). Moreover, to perform a precise measurement an acidic treatment is also recommended to remove the carbonates from the samples, by this way only the organic carbons are remaining to be oxidized. Existing cleaning procedures include multiple chemical processes which are often time-consuming and skill-intensive, and involve the use of cleaning agents and/or acidic reactants that are expensive, corrosive, and difficult to transport, handle, and store. If the cleaning procedure does not completely remove the contaminants, a bias will likely occur on the TOO value.

To minimize the chances of a bias (i.e., underestimation or overestimation) on the TOC values in drill cuttings, determination of the TOC of drill cuttings is performed at the laboratory level where the appropriate chemical and/or thermal cleaning treatment of the drill cuttings is carried out prior to measuring the TOC. Whatever the cleaning procedure used, cleaning, processing, and analysis of drill cutting samples according to existing methods effectively precludes providing a real-time analysis of TOC in drill cuttings in the field, because existing methods employ lengthy and complicated cleaning, preparation, testing, and interpretation procedures which are expensive, time-consuming, and skill-intensive.

SUMMARY

This summary is provided to introduce a selection of concepts that are further described in the detailed description. This summary is not intended to be used as an aid in limiting the scope of the claimed subject matter.

In one aspect, embodiments of the present disclosure are directed to a computer system which includes an input port, an output port, and a processor coupled with the input and output ports and executing processor-executable code stored in a non-transitory processor-readable medium. The processor-executable code causes the processor to receive a signal via the input port, the signal including data indicative of an amount of combustion products produced by a sample of drill cuttings subjected to an oxidation reaction at a substantially constant temperature as a function of time. The drill cuttings are obtained from a well-bore. The processor-executable code further causes the processor to process the data with a predetermined logic according to the substantially constant temperature to: (a) locate peaks in the amount of combustion products, the peaks produced by the sample of drill cuttings at a set of instants in time; (b) correlate the set of instants in time with the presence of at least one of organic carbon compounds from a contaminant present in the sample of drill cuttings, organic carbon compounds present in the sample of drill cuttings, and inorganic carbon compounds present in the sample of drill cuttings; and (c) calculate at least one of an amount of contaminant present in the sample of drill cuttings, a total amount of organic carbon compounds present in the sample of drill cuttings, and a total amount of inorganic carbon compounds present in the sample of drill cuttings, partially based on the peaks. The processor-executable code also causes the processor to output a signal indicative of at least one of the amount of contaminant present in the sample of drill cuttings, the total amount of organic carbon compounds present in the sample of drill cuttings, and the total amount of inorganic carbon compounds present in the sample of drill cuttings via the output port.

In another aspect, embodiments of the present disclosure are directed to an isothermal analysis system comprising an analyzer including a furnace having a sample chamber for receiving a sample of drill cuttings obtained from a well-bore, a controller coupled with the furnace so as to maintain substantially constant temperature inside the furnace and a detector for detecting the amount of at least one combustion product produced by the sample subjected to an oxidation reaction in the furnace as well as a computer system as defined above.

In another aspect, embodiments of the present disclosure are directed to a method, including: (a) receiving a signal via an input port by a processor executing processor-executable code stored in a non-transitory processor readable medium, the signal including data indicative of an amount of a combustion product produced by a sample of drill cuttings subjected to a combustion reaction at a substantially constant temperature and as a function of time; (b) processing the data by the processor with a predetermined logic stored in a non-transitory processor-readable medium to locate a peak in the amount of the combustion product produced by the sample of drill cuttings and calculate a total amount of organic carbon present in the sample of drill cuttings; and (c) outputting, by the processor via an output port, a signal indicative of the total amount of organic carbon compounds present in the sample of drill cuttings.

In another aspect, embodiments of the present disclosure are directed to a method, including (a) heating a sample chamber of a furnace to a temperature regulated to a substantially constant temperature, (b) placing a sample of drill cuttings obtained from a well-bore into the sample chamber, (c) detecting the amount of at least one combustion product produced by the sample subjected to the oxidation reaction inside of the furnace, (d) transmitting a signal to an input port of at least one processor executing processor-executable code stored in a non-transitory processor readable medium, the signal including data indicative of an amount of said combustion products as a function of time, (e) processing the data by the at least one processor with a predetermined logic stored in a non-transitory processor-readable medium to locate at least one peak in the amount of the at least one combustion product produced by the sample of drill cuttings and calculate a total amount of organic carbon present in the sample of drill cuttings and (f) outputting, by the at least one processor via an output port, at least one signal indicative of the total amount of organic carbon compounds present in the sample of drill cuttings.

In a further aspect, embodiments of the present disclosure are directed to a method, including: (a) heating a sample chamber of a furnace to a temperature within a range from 500° C. to 1100° C. and which is regulated to a substantially constant temperature; (b) placing a known amount of a sample containing organic carbon into the sample chamber; and (c) actuating a processor to determine a total amount of organic carbon present in the sample using a time-based analysis of combustion products detected from the sample.

In a further aspect, of the present disclosure are directed to a sample preparation method for preparing drill cuttings extracted from a well-bore to an analysis method, consisting in part or all of the following:
drying the cuttings of the sample,
grinding the cuttings of the sample,
sieving the cuttings of the sample, and
weighing the sample.

For avoidance of doubt, it is reminded that "consists in" means that the sample preparation method does not comprise any other step than the ones defined above, and in particular no cleaning of the drill cuttings with a cleaning fluid or a solvent.

BRIEF DESCRIPTION OF THE DRAWINGS

Certain embodiments of the present disclosure will hereafter be described with reference to the accompanying drawings, wherein like reference numerals denote like elements, and.

DETAILED DESCRIPTION

Figure 1:
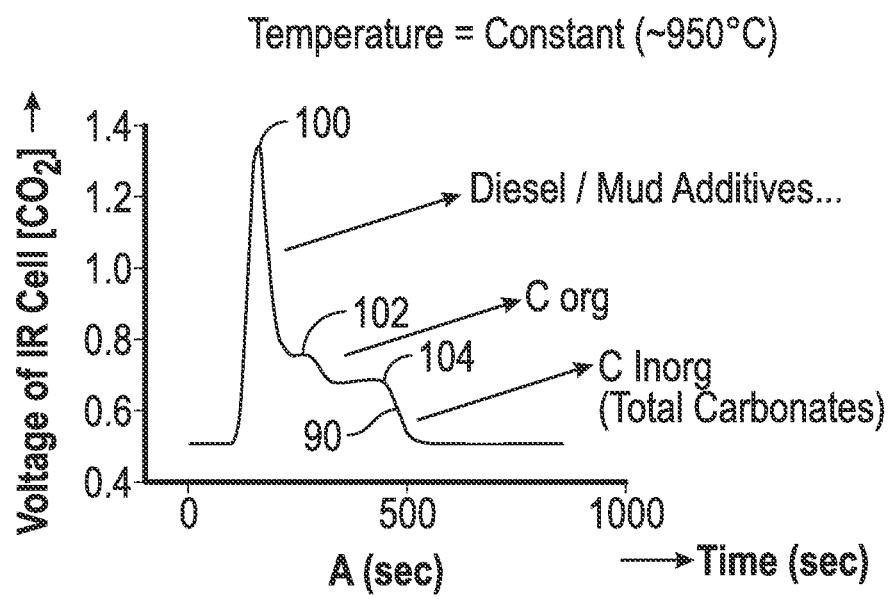
FIG. 1 is a graph showing peaks within a time-based output of a detector obtained via a high-temperature isothermal analysis method analyzing drill cuttings drilled with oil-based drilling mud according to embodiments of the present disclosure.

Embodiments of the present disclosure will now be described in detail with reference to the accompanying drawings. Further, in the following detailed description of embodiments of the present disclosure, numerous specific details are set forth in order to provide a more thorough understanding of the disclosure. However, it will be apparent to one of ordinary skill in the art that the embodiments disclosed herein may be practiced without these specific details. In other instances, well-known features have not been described in detail to avoid unnecessarily complicating the description.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is apparent that it is meant otherwise.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment, although the inventive concepts disclosed herein are intended to encompass combinations and permutations of the features of the embodiments described herein.

Further, a "sample" as described herein may be a drill cutting obtained from a wellbore, or another type of sample in which the presence or organic and/or inorganic carbons are to be analyzed and/or quantified. For example, a "sample" could be dirt obtained from a field or a liquid part such as the drilling fluid.

As used herein "drill cuttings" or "drill cuttings sample" are intended to include solid material such as rocks, soil, sand, sediment, minerals, kerogen, fragments, drill cores, and other solid components derived from a borehole as a result of drilling operations.

As used herein, "contaminated drill cuttings" refers to drill cuttings contaminated with one or more solid, semi-solid, or liquid contaminant, such as organic carbon compounds, oil-based drilling mud, polymers, or combinations thereof.

Some embodiments of the present disclosure are generally directed to isothermal analysis systems and methods configured to accurately measure the TOC of drill cuttings substantially in real time and without cleaning the drill cuttings prior to measuring the TOC.

Isothermal analysis systems and methods according to embodiments of the present disclosure may be implemented with an analyzer configured to incinerate carbon material of drill cuttings at substantially constant temperature in a controlled atmosphere; generate measured data indicative of the detection of a volume or amount of at least one combustion product from the drill cuttings (e.g., typically carbon dioxide, carbon monoxide or others such as $H_2O$, $NO_2$, or $SO_2$); and analyze the measured data to determine the TOC of the drill cuttings (or the total sulfur content, the total nitrogen content depending of the detector used).

Some embodiments of the present disclosure relate to the preparation of drill cutting samples in which the TOC will be measured followed by the calculation of the TOC by an isothermal analysis system that can be applied on-site (e.g., at the well-site). By using isothermal analysis systems and methods according to embodiments of the present disclosure, TOC can be measured in real-time by an operator or technician on-site.

In some embodiments, isothermal analysis methods according to the present disclosure include generating measured data indicative of at least the total carbons present in a sample of drill cuttings or soil followed by a mathematical treatment of the measured data. The TOC of the sample of drill cuttings is calculated with the measured data without using contributions to the measured data resulting from carbons originating from contaminants present in the sample of drill cuttings. The measured data may be plotted as a waveform that may be referred to herein as a "thermal fingerprint". The methods disclosed herein enable users to analyze the thermal footprint or fingerprint for a particular sample and distinguish the presence of first carbons originating from the contamination present in the sample of drill cuttings from the presence of second carbons originating from organic (kerogens) and inorganic compounds present in the sample of drill cuttings via a high-temperature isothermal analysis (e.g., at 1000° C., or at a constant temperature between about 900° C. and 1100° C.). As a result, the measurement of TOC in contaminated or uncontaminated drill cuttings may be an automatic procedure that can be rapidly executed on-site and optionally without any dedicated sample preparation or operator expertise.

Some embodiments of the present disclosure are directed to a reliable direct measurement of TOC of type(s) of solid samples (drill cuttings, soils, crushed rocks, or other solids), without cleaning procedures using dangerous solvents (e.g., pentane, hexane, toluene) or pre-heating the samples in order to burn off contaminants present in the solid sample (e.g., combustion of mud additives). The drill cuttings may be ground up and weighed before an analysis, without removal of contaminants. For example, the sample preparation and cleaning in the prior methodologies may be omitted in some embodiments of the present disclosure. Embodiments of the present disclosure allow for generating a log in real time of TOC values, TIC values, and other parameters and reporting or otherwise providing the log to a user.

Figure 2:
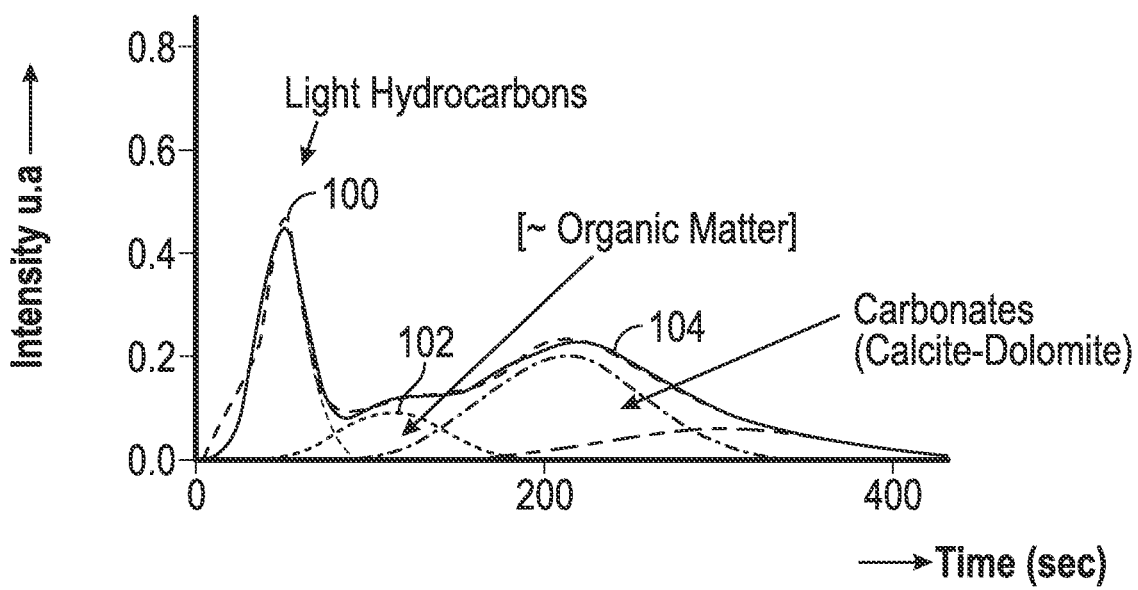
FIG. 2 is a graph showing mathematical modeling to evaluate carbon contributions by peaks and valleys for the graph of FIG. 1 according to embodiments of the present disclosure.

Referring now to FIGS. 1-2, shown therein are time-based waveforms of levels of combustion components collected from drill cutting samples subjected to a high-temperature isothermal analysis at a constant temperature of about 1000° C. or a constant temperature between about 900° C. and about 1100° C. (e.g., 1000° C.±100° C.) in a controlled atmosphere. For the high-temperature isothermal analysis, the drill cutting samples may include three main carbons compound components—the carbon components from light hydrocarbons (e.g., from contaminants), the carbon compounds from heavy hydrocarbons (e.g., kerogens, bitumens and others present in the drill cuttings) and the inorganic carbon compounds (e.g., from the carbonates present in the drill cuttings). By incinerating the sample at a relatively high and constant temperature such as 1000° C. (±100° C.) in a controlled atmosphere, it is possible to distinguish the three types of carbon compounds that are present in a sample of drill cuttings including the amounts and contributions of each type of carbon compound by analyzing the time-based waveforms as will be explained in more detail below. Typically a temperature such as 1000° C. (±100° C.) is suitable to combusted most of the carbons types and consequently distinguish the three contributions as described herein.

Isothermal analysis methods and systems according to some embodiments of the present disclosure make the following assumptions regarding peaks in a waveform 90 produced by detection of combustion products from a sample of contaminated drill cuttings subjected to an environment being typically 1000° C. in a high-temperature isothermal analysis according to the present disclosure. The waveform 90 includes a first peak 100, a second peak 102 and a third peak 104. The first peak 100 is the earliest peak observed at a first set of instants in time and corresponds to, or is correlated with, a presence of light volatile hydrocarbon compounds and may also indicate a presence of carbon compounds from other contaminants or pollutants such as diesel and/or mud additives present in the drill cuttings sample. The second peak 102 is observed at a second set of instants in time later than the first peak 100 and is attributed to combustion products that are indicative of a presence of carbon compounds coming mainly from organic materials such as the kerogen and bitumen. A level of the waveform 90 at the second peak 102 is indicative of an amount of the TOC present in the sample of contaminated drill cuttings. The third peak 104 of the waveform 90 is observed at a third set of instants in time subsequent to the second peak 102 and is attributed to, or otherwise correlated with, the presence of inorganic carbon compounds in the sample of drill cuttings such as carbonates from calcite and/or dolomite and may also be indicative of the amount of TIC present in the sample of drill cuttings.

In some instances, isothermal analysis methods and systems according to the present disclosure result in waveforms indicative of a unique thermal fingerprint of the sample of drill cuttings allowing users to compare different drill cuttings together and to extract and calculate TIC and TOC. Any suitable mathematical curve (e.g., a Gaussian curve) may be used in some embodiments of the present disclosure to plot the measured data. For example, a theoretical curve may be derived where the contribution of each peak regarding the total signal is calculated and assigned. Because pollutants from the drilling fluids (e.g., diesel, other organic carbon mud additives and/or light volatile molecules) are expected to react faster than other carbon compounds in the sample of drill cuttings, the detection of combustion products indicating the presence of pollutants are assimilated mainly into the first peak 100. Similarly, the organic carbon compounds present in the sample of drill cuttings such as kerogens are expected to react slower than the pollutants such that the detection of combustion products indicating the presence of organic carbon compounds are assimilated mainly into the second peak 102. Finally, inorganic carbon compounds present in the sample of drill cuttings are expected to react slower than all the organic compounds such that the detection of combustion products indicating the presence of inorganic carbon compounds are assimilated mainly into the third peak 104. The amounts and composition of the contaminants, organic compounds and inorganic compounds will affect the shape of the waveform 90 thereby providing the thermal fingerprint. The waveforms 90 can be stored, analyzed and compared to other waveforms so as to identify amounts and compositions of contaminants, organic compounds and inorganic compounds that are present within the drill cutting samples.

In the embodiment of FIG. 2, where drill cuttings were drilled using oil-based drilling mud, the impact of the drilling fluid may be subtracted as follows. The contribution of the earliest peak 100 may be mathematically modeled by any suitable function and removed from the entire signal. Once the contribution of the contaminants has been accounted for, the TOC may be the TC measured. The oil based mud mainly includes relatively light volatile hydrocarbon compounds which are expected to appear in one peak. Thus, the calculation may be TC=TOC and TIC=Σ(all peaks)−contribution of the peak appearing first in time relative to the rest of the observed peaks. In this instance where four peaks are observed, TOC=[Σ(all peaks: 100, 102, 104)]−(peak 100).

To produce this response, a controlled isothermal reaction at a constant temperature is used in some embodiments, by rapidly introducing a sample of drill cuttings to a substantially constant temperature being either about 650° C. (low-temperature isothermal analysis method where mainly the organic matter reacts) or about 1000° C. (high-temperature isothermal analysis method where all carbon types will react, organic and inorganic). For example, the sample of drill cuttings may be rapidly introduced or positioned into a pre-heated furnace while the furnace is maintained at a substantially constant temperature being either about 1000 (or between about 900° C. and about 1100° C.) or about 650° C. (e.g., between about 500° C. and 750° C.), respectively for the high-temperature isothermal analysis method and the low-temperature isothermal analysis method according to the present disclosure.

The difference between the high-temperature isothermal analysis and the low-temperature isothermal analysis being the data analysis and the type of thermal fingerprint produced by the samples. For low-temperature isothermal analysis according to the present disclosure, there is no likely or expected contribution of the main inorganic carbonates such as calcite and dolomite. The temperature of the low-temperature isothermal analysis of about 650° C. (or between 550° C. and 750° C.) is too low to start significantly the decomposition process of the inorganic carbon, and as a consequence the signal recorded is dedicated to the organic carbon compounds (e.g., there is substantially no carbonate contribution in the signal). The principle of the isothermal analysis system and methods according to the present disclosure is the same for both the high-temperature isothermal analysis and the low-temperature isothermal analysis, and accordingly the first peak is attributed to lighter volatile molecules in the sample. For low-temperature isothermal analysis according to the present disclosure, if the sample includes oil-based mud drill cuttings, the first peak will be attributed to the contamination and mathematically removed from the TOC calculations, and the remaining peaks will be indicative of one or more different types of organic carbons present in the sample.

A suitable detector coupled with the pre-heated furnace detects and records a signal indicative of an amount of at least one combustion product produced by the sample of drill cuttings as a function of time. It is to be understood that any suitable method or device configured to heat a sample of drill cuttings or other solids to a substantially constant temperature being either around 650° C. (±100° C.) for the low-temperature isothermal analysis or around 1000° C. (±100° C.) for the high-temperature isothermal analysis implemented with embodiments of the present disclosure.

Some embodiments of isothermal analysis according to the present disclosure do not include cleaning or removal of carbonates from a sample of drill cuttings to accurately measure TOC in the sample of drill cuttings, because a mathematical model is implemented to separate (e.g., by a deconvolution process) individual peaks which are correlated with a type of carbon compound present in the sample of drill cuttings or with contaminants contaminating the sample of drill cuttings. Further, by using a suitable mathematical model (e.g., implemented as software or processor-executable instructions stored in a non-transitory processor-readable medium and executed by at least one processor), the time of isothermal analysis is reduced by avoiding a programmed gradual heating of the sample to remove organic carbon contaminants.

Figure 3:
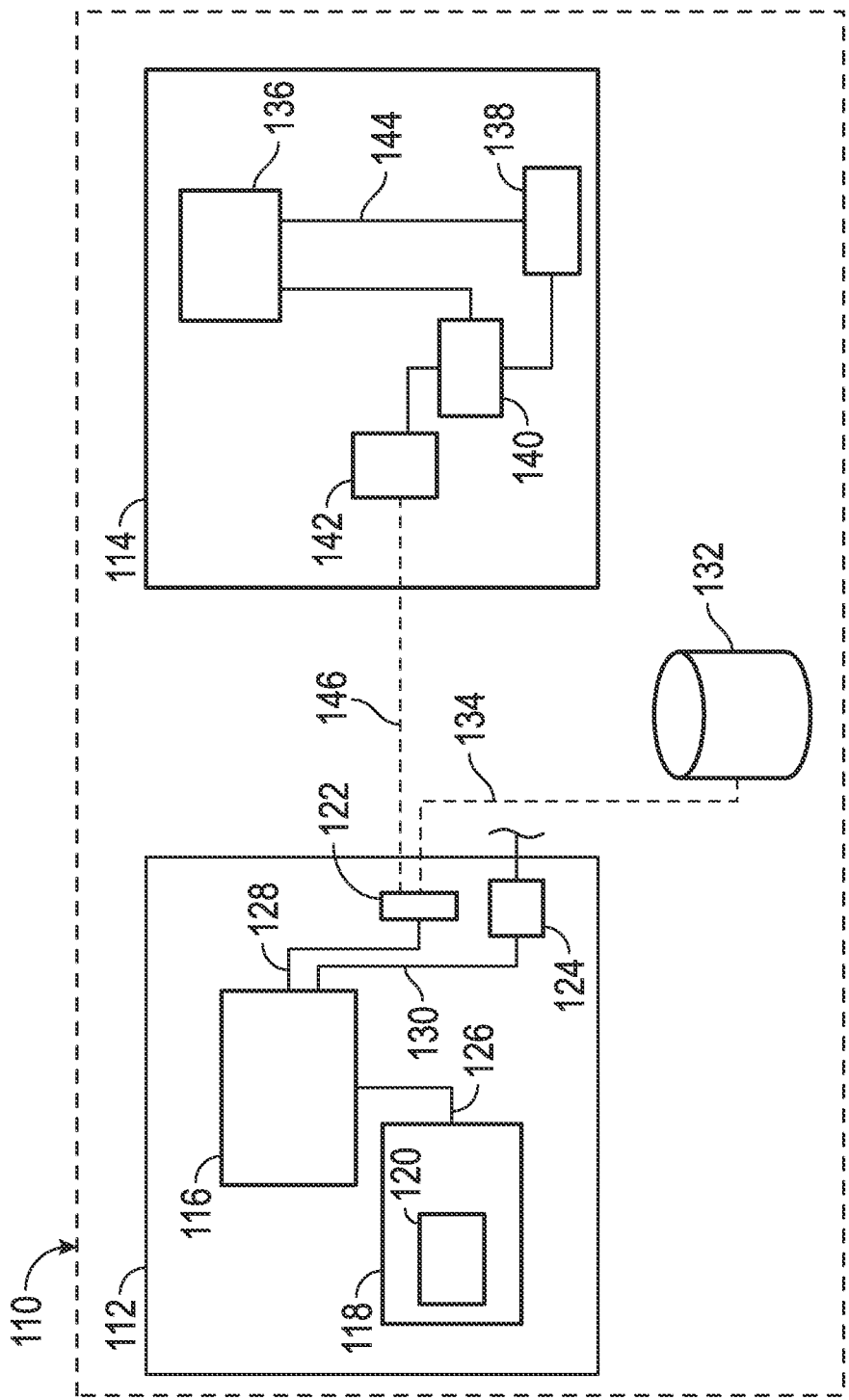
FIG. 3 is a diagram of an isothermal analysis system according to some embodiments of the present disclosure.

Referring now to FIG. 3, shown therein is an isothermal analysis system 110 according to some embodiments of the present disclosure. The isothermal analysis system 110 includes a computer system 112 and an analyzer 114.

The computer system 112 includes at least one processor 116, one or more non-transitory processor readable medium 118 storing processor executable code 120, an input device 122, and an output device 124.

The processor 116 may be implemented as a single processor or multiple processors working together or independently to execute the processor executable code 120 described herein. Embodiments of the processor 116 may include a digital signal processor (DSP), a central processing unit (CPU), a microprocessor, a multi-core processor, and combinations thereof. It is to be understood that in certain embodiments using more than one processor 116, the processors 116 may be located remotely from one another, located in the same location, or comprise a unitary multicore processor, for example.

The processor 116 is coupled to and communicates with the non-transitory processor readable medium 118 via a path 126 which can be implemented as a data bus, for example. The processor 116 may communicate with the input device 122 and the output device 124 via paths 128 and 130, respectively. Paths 128 and 130 may be implemented similarly to, or differently from path 126. For example, the paths 128 and 130 may be the same type of data bus as the path 126 or different type of data bus. The processor 116 further communicates bi-directionally with a database system 132 via a path 134.

The non-transitory processor readable medium 118 stores processor executable code 120 and may be implemented as random access memory (RAM), a hard drive, a hard drive array, a solid state drive, a flash drive, a memory card, a CD-ROM, a DVD-ROM, a BLU-RAY, a floppy disk, an optical drive, and combinations thereof. When more than one non-transitory processor readable medium 118 is used, one of the non-transitory processor readable mediums 118 may be located in the same physical location as the processor 116, and another one of the non-transitory processor readable mediums 118 may be located in location remote from the processor 116. The physical location of the non-transitory processor readable mediums 118 can be varied and the non-transitory processor readable medium 118 may be implemented as a "cloud memory," i.e. non-transitory processor readable medium 118 which is partially or completely based on or accessed using a computer network (e.g., the Internet). In one embodiment, the non-transitory processor readable medium 118 may store a database accessible by the processor 116. In this embodiment, the non-transitory processor readable medium 118 may also store data collected by the analyzer 114 as will be described below.

The input device 122 bi-directionally exchanges signals and/or data with the processor 116, and can be implemented as a computer port, a wireless port, a data bus, a keyboard, a mouse, a network adapter, a touch screen, a digital port, an optical port, a wireless port, an Ethernet port, a USB port, a virtual port, and combinations thereof.

The output device 124 bi-directionally exchanges information with the processor 116 and may transmit information from the processor 116 to a user or to another processor coupled with the output device 124, such that the information can be perceived by the user or received by another processor. For example, the output device 124 may be implemented as a computer port, a physical port, a virtual port, a server, a computer monitor, a cell phone, a tablet, a speaker, a website, a PDA, a fax, a printer, a projector, a laptop monitor, a wireless modem, a digital subscriber line modem, a cable modem, a network bridge, an Ethernet switch, a direct wired connection, a display, or any other suitable communications device capable of communicating signals and/or data between the processor 116 and a user and/or a device or processor coupled with the output device 124.

The database system 132 may include one or more processors, one or more non-transitory computer readable medium, and computer executable instructions including database software and measured data (which may be relational data) indicative of correlations between sets of instants in time, temperatures and at least one of organic contaminant present in a sample of drill cuttings, organic carbon present in the sample of drill cuttings and also inorganic carbon present in the sample of drill cuttings if the temperature of the method used is about 1000° C. (e.g., in the high-temperature isothermal analysis), as will be described below. The non-transitory computer readable medium can take many forms, such as random access memory (RAM), a hard drive, a hard drive array, a solid state drive, a flash drive, a memory card, a CD-ROM, a DVD-ROM, a BLU-RAY, a floppy disk, an optical drive, and combinations thereof. The path 134 may be a data bus, or may be a non-continuous path, such as through a computer network, a wireless path, a cable, a dock, or combinations thereof.

The processor 116 reads and/or executes the processor executable code 120 and/or creates, reads, manipulates, alters, and stores computer data structures into the non-transitory processor readable medium 118 and/or into the non-transitory computer readable medium of the database system 132. The processor executable code stored in the non-transitory processor readable medium 118 and/or in the database system 132 may be written in any suitable programming language, such as C++, C#, Java, or Python, for example.

The analyzer 114 includes a furnace 136, a detector 138, a controller 140, and an output device 142.

The furnace 136 may be implemented as any desired furnace having an enclosure defining a sample chamber configured to reach and maintain a substantially constant temperature from about 500° C. to about 1100° C., for example, and may include a door or sample port to allow inserting a sample of solids or drill cuttings into the sample chamber of the furnace 136. Further, the furnace 136 may be configured to allow constant airflow therethrough in some embodiments. Any suitable heat source, such as an electric resistive heater, may be used to heat the furnace 136.

The detector 138 may be operatively coupled with the furnace 136 (e.g., via a path 144 such as a data bus) and in communication with the sample chamber (either directly or indirectly) so as to detect an amount of at least one combustion product (e.g., CO, $CO_2$) given off or produced by a sample of drill cuttings or solids positioned in the furnace 136 as a function of time. In some embodiments, the detector 138 may be incorporated into a flue of the furnace 136.

The detector 138 may be implemented as an infrared detector in some embodiments, and may be coupled with the controller 140 and/or with the processor 116 (e.g., via the input device 122) so that data may be exchanged between the processor 116 and the detector 138. In some embodiments, the detector 138 may provide an output signal (in electronic or optical form) indicative of an amount of at least one combustion product as a function of time to the controller 140 and/or to the processor 116 via the output device 142 communicating with the input device 122 via a path 148 (e.g., a data bus, a cable, a wireless connection). In some embodiments, the detector 138 may be configured to initiate or begin detecting the at least one combustion product produced by a sample at the same time as the sample is introduced into the sample chamber, or substantially immediately thereafter. For example, any suitable automated switch may be activated by closing the sample chamber or by inserting the sample of drill cuttings into the sample chamber to initiate the detection of combustion products by the detector 138 in some embodiments.

The controller 140 is coupled with the furnace 136 and with the detector 138, and is configured to control the temperature inside the furnace 136, so as to maintain a substantially constant temperature inside the furnace 136. The controller 140 may receive the output signal indicative of the amount of at least one combustion product as a function of time from the detector 138 via a path 146 (e.g., a data bus). The controller 140 may include a processor coupled with a non-transitory processor-readable medium and executing processor-readable code to filter, amplify, store, or otherwise process signals and/or data received form the detector 138. In some embodiments, the controller 140 may store information from the signals received from the detector 138 in a non-transitory processor-readable medium. Further, in some embodiments, the controller 140 may transmit data indicative of the signals received from the detector 138 to the processor 116 via the output device 142 sending one or more signals to the input device 122 via the path 146.

It is to be understood that the computer system 112 and/or the analyzer 114 may be located at a well-site, or may be located remotely from one another and/or from the well-site in some embodiments of the present disclosure. Further, in some embodiments, the computer system 112 and the analyzer 114 may be implemented as an integrated system, or may exchange data and/or signals with one another over a computer network such as the Internet, a LAN, a cellular network, a satellite network, a wireless network, or combinations thereof. In some embodiments, the computer system 112 and the analyzer 114 may be implemented as a unitary device.

Figure 4:
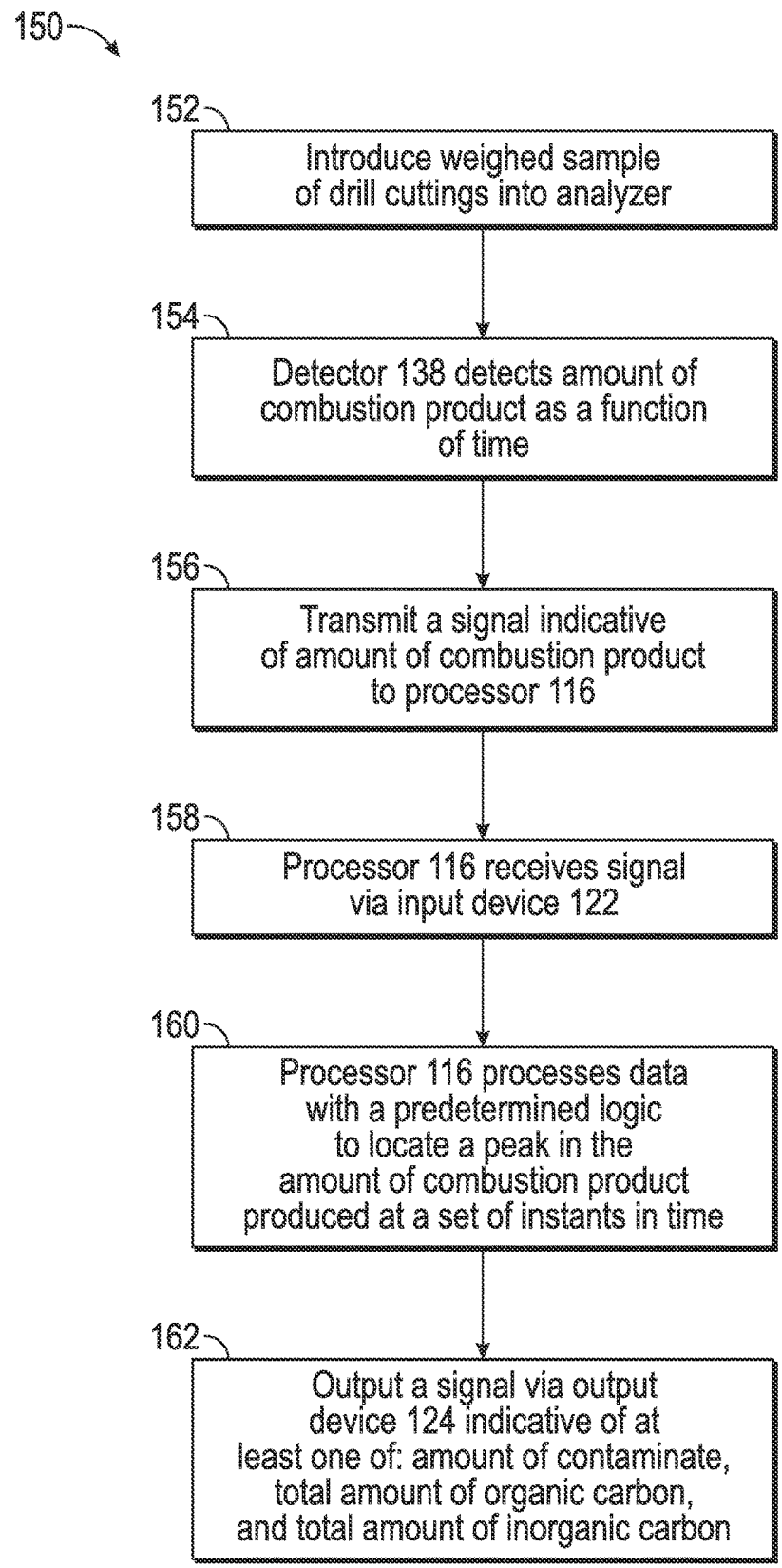
FIG. 4 is a diagram of an isothermal analysis method according to some embodiments of the present disclosure.

Referring now to FIG. 4, an isothermal analysis method 150 for analyzing drill cuttings using the isothermal analysis system 110 according to the present disclosure is shown. The method 150 is applicable with any analyzers such as the analyzer 114 where a high temperature oxidation reaction methodology is coupled with one or many detectors such as the detector 138 (e.g., infrared sensor). The detector 138 generates time based data and the data is analyzed by a mathematical model by the computer system 112 to evaluate the contribution of each carbon compound based on the following hypothesis: different types of carbons subjected to a constant temperature will oxidize and generate combustion products at different times. When the sample, containing some organic matter and carbonates, is contaminated by mud additive such as diesel, at least three peaks will exist in the data and be located at different instants of time. In some embodiments where the method 150 is implemented for a high-temperature isothermal analysis the constant temperature may be about 1000° C.+/−100° C., and a first peak may be interpreted as representing combustion products generated from the oxidation of the contamination included with the drill cuttings, a second peak may be interpreted as representing combustion products generated from the oxidation of carbon from the organic matter in the drill cuttings, and a third peak may be interpreted as representing combustion products generated from the decomposition of the carbonates present in the drill cuttings by the isothermal analysis system 110 according to some embodiments of the present disclosure.

Similarly, where the method 150 is implemented for low-temperature isothermal analysis where the constant temperature is about 650° C. (±100° C.), the detector 138 generates time based data and the data is analyzed by a mathematical model by the computer system 112 to evaluate the contribution of each carbon based on the following hypothesis: different types of organic matter subjected to a constant temperature will oxidize and generate a specific fingerprint at 650° C. (±100° C.). The TOC is calculated and all peaks are attributed to a particular type of carbon from the organic matter, following the same statement where the first peak corresponds to lighter volatile carbon compounds compared to the other heavier carbon compounds present in the sample.

In some embodiments, a user may rapidly introduce a weighed (e.g., a known amount of) sample of drill cuttings into the furnace 136 of the analyzer 114 as indicated in a block 152. The furnace 136 may be heated and regulated to a constant and known temperature which can be 1000° C. (±100° C., for high-temperature isothermal analysis) or 650° C. (±100° C., for low-temperature isothermal analysis). The drill cuttings may be obtained from a well bore in some embodiments of the present disclosure and may be contaminated with drilling mud or the like. For example, in some embodiments, a sample chamber of the furnace 136 may be heated to a temperature being either 1000° C. (±100° C. for high-temperature isothermal analysis) or 650° C. (±100° C. for low-temperature isothermal analysis). In some embodiments, the sample of drill cuttings may be rapidly introduced in the furnace 136 such that the temperature of the sample chamber of the furnace 136 may be regulated so as not vary by more than 1% as the sample is being introduced in the furnace 136 or as a result of introducing the sample in the furnace 136. Further, the sample of drill cuttings may include contaminated drill cuttings which may not be cleaned prior to being introduced in the furnace 136, in some embodiments of the present disclosure.

As shown by block 154, the detector 138 detects amounts of the at least one combustion product produced by the sample of drill cuttings which may vary as a function of time. In some embodiments, the sample of drill cuttings may be introduced in the furnace 136 at a first instant of time, and the detector 138 may detect amounts of the at least one combustion product produced by the sample of drill cuttings at a second instant of time which may be earlier, later, or may occur simultaneously with the first instant in time, for example.

As shown by block 156, the detector 138 may transmit at least one signal indicative of data of the amount of at least one combustion product produced by the sample of drill cuttings as a function of time to the processor 116 via the path 146.

As shown by block 158, the processor 116 may receive the at least one signal via the input device 122.

As shown by block 160, the processor 116 may process the data with a predetermined logic (e.g., using a time-based analysis of combustion products detected from the sample of drill cuttings) stored in the non-transitory processor readable medium 118 to locate at least one peak in the amount of the at least one combustion product, the at least one peak produced by the sample of drill cuttings at a set of instants in time depending on the method used (e.g., high-temperature isothermal analysis or low-temperature isothermal analysis). The processor 116 may correlate the set of instants in time to determine the presence of at least one of an organic contaminant in the sample of drill cuttings, organic carbon compounds in the sample of drill cuttings for the low-temperature isothermal analysis, and additionally inorganic carbon compounds in the sample of drill cuttings for the high-temperature isothermal analysis, and consequently calculate at least one of an amount of contaminant present in the sample of drill cuttings, a total amount of organic carbon compounds present in the sample of drill cuttings, and a total amount of inorganic carbon compounds present in the sample of drill cuttings.

As shown by block 162, the processor 116 may output via an output device 124 at least one signal indicative of the at least one of the amount of contaminant present in the sample of drill cuttings, the total amount of organic carbon compounds present in the sample of drill cuttings, and also the total amount of inorganic carbon compounds present in the sample of drill cuttings depending of the temperature used (e.g., for the high-temperature or the low-temperature isothermal analysis).

In some embodiments, the processor 116 may further provide a real-time log of the TOC and TIC present in the sample of drill cuttings to a user via the output device 124.

Figure 5:
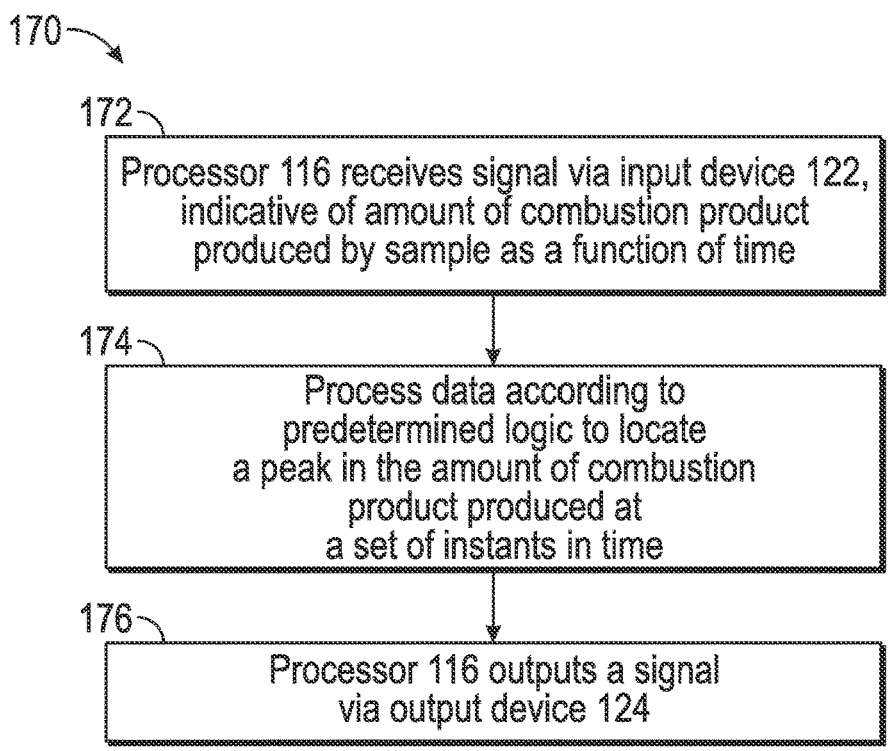
FIG. 5 is a diagram of an isothermal analysis method for measuring at least the total organic carbon of drilled cuttings according to some embodiment of the present disclosure.

Referring now to FIG. 5, an embodiment of an isothermal analysis method 170 carried out by the isothermal analysis system 110 according to the present disclosure is shown.

As shown by block 172, the processor 116 receives a signal via the input device 122, the signal including data indicative of an amount of at least one combustion product produced by a weighed (e.g., a known amount) sample of drill cuttings subjected to an oxidation reaction at a substantially constant temperature as a function of time, the drill cuttings being obtained from a well bore. In some embodiments the drill cuttings may be substantially solid. Further, in some embodiments, the constant temperature may be between about 500° C. and 750° C. (e.g., for a low-temperature isothermal analysis using a constant temperature of about 620° C.), or may be between 900° C. and 1100° C. (e.g., for a high-temperature combustion analysis using a constant temperature of about 985° C.).

As shown by block 174, the processor 116 may process the data according to a predetermined logic to locate at least one peak in the amount of the at least one combustion product, the at least one peak produced by the sample of drill cuttings at a set of instants in time. The processor 116 may correlate the set of instants in time with the presence of at least one of organic carbon compound from at least one contaminant in the drill cuttings, organic carbon compounds in the sample of drill cuttings, and depending on the temperature used (e.g., the high-temperature or the low-temperature isothermal analysis), inorganic carbon compounds in the sample of drill cuttings, and consequently calculate at least one of an amount of organic contaminant present in the sample of drill cuttings, a total amount of organic carbon compounds present in the sample of drill cuttings, and a total amount of inorganic carbon compounds present in the sample of drill cuttings, at least partially based on the at least one peak.

In some embodiments, the set of instants in time may be a first set of instants in time, and the processor 116 may correlate the first set of instants in time with at least one of the organic carbon compound from at least contaminant present in the sample of drill cuttings, the organic carbon compounds present in the sample of drill cuttings, and the inorganic carbon compounds present in the sample of drill cuttings by accessing data stored in the database system 132 indicative of a second set of instants in time correlated with the at least one of the organic contaminant present in the sample of drill cuttings, the organic carbon compounds present in the sample of drill cuttings, and the inorganic carbon compounds present in the sample of drill cuttings. The second set of instants in time may at least partially overlap with the first set of instants in time.

In some embodiments, the processor 116 may process the data according to a predetermined logic to locate at least one first peak produced by the sample of drill cuttings at a first set of instants in time correlated with organic carbon compounds present in the sample of drill cuttings and at least one second peak produced by the sample of drill cuttings at a second set of instants in time correlated with inorganic carbon compounds present in the sample of drill cuttings, the second set of instants in time being later than the first set of instants in time.

Further, in some embodiments, the processor 116 may process the data according to a predetermined logic to define at least one first peak produced by the sample of drill cuttings at a first set of instants in time correlated with organic carbon compounds present in at least one contaminant in the sample of drill cuttings and at least one second peak produced by the sample of drill cuttings at a second set of instants in time correlated with organic carbon compounds present in the sample of drill cuttings, the first set of instants in time being earlier than the second set of instants in time.

Further, in some embodiments, the at least one peak may be a first peak and the set of instants in time may be a first set of instants in time, and the processor 116 may locate at least one second peak in the amount of the at least one combustion product, the second peak produced by the sample of drill cuttings at a second set of instants in time later than the first set of instants in time, correlate the first set of instants in time with an organic carbon compound from a contaminant present in the sample of drill cuttings, and the second set of instants in time with organic carbon compounds present in the sample of drill cuttings, and calculate a total amount of organic carbon compounds present in the sample of drill cuttings, at least partially based on the first and second peaks.

As shown by block 176, the processor 116 may output at least one signal indicative of at least one of the amount of organic contaminant present in the sample of drill cuttings, the total amount of organic carbon compounds present in the sample of drill cuttings, and the total amount of inorganic carbon compounds present in the sample of drill cuttings via the output device 124.

Figure 6:
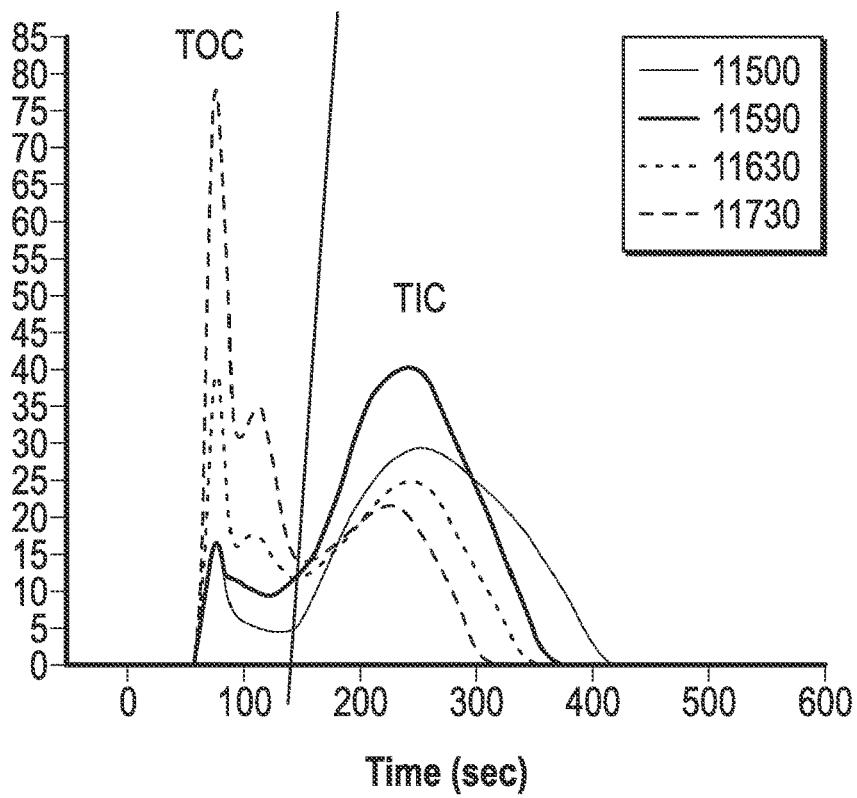
FIG. 6 is a graph showing superposition of samples of drill cuttings from various well-bore depths analyzed at 1000° C. (±100° C.) via a high-temperature isothermal analysis according to some embodiments of the present disclosure where the total organic carbon (TOC) and the total inorganic carbon (TIC) are specified as a function of time.

Referring now to FIG. 6, in one embodiment of a high-temperature isothermal analysis, the isothermal analysis system 110 was operated with the furnace 136 heated to 985° C., to have a substantially complete carbon content of a sample of drill cuttings, because any organic carbon (TOC) and inorganic carbon (TIC) would combust at this temperature.

Multiple weighed samples of drill cuttings from several well-bore depths in the form of a powder sieved typically under 150 μm were placed rapidly (e.g., so as to minimize chances of affecting the temperature inside the furnace 136) into a heated furnace 136 at 985° C. in order to have a rapid thermal degradation of the organic and inorganic carbons in the sample of drill cuttings so as to carry out a high-temperature isothermal analysis according to the present disclosure. Under a constant flow of air, the sample of drill cuttings was combusted so that the organic carbon reacted into $CO_2$ and $H_2O$, and the inorganic carbon reacted into $CO_2$. Because of thermal degradation kinetics, most organic carbons in the drill cuttings were expected to be degraded and transformed earlier than the inorganic carbons present in the drill cuttings.

As shown in FIG. 6, an example of superposition of multiple samples of drill cuttings from various well-bore depths analyzed by the isothermal analysis system 110 according to the present disclosure, where many peaks have been identified and two zones related to the carbon types (organic and inorganic) have been defined by some methods according to the present disclosure. In this instance, the inorganic carbons are mainly coming from calcite and dolomite, and start to react at a set of instants in time around 125±25 seconds after the beginning of the reaction (e.g., after the sample of drill cuttings is placed inside the furnace 136). Effectively, the decomposition of the two carbonates corresponds to:

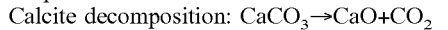
Calcite decomposition: $CaCO_3 \rightarrow CaO + CO_2$
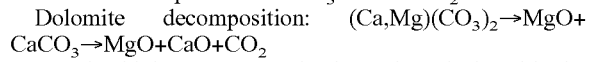
Dolomite decomposition: $(Ca,Mg)(CO_3)_2 \rightarrow MgO + CaCO_3 \rightarrow MgO + CaO + CO_2$ For the high-temperature isothermal analysis with the furnace 136 at a temperature of about 1000° C. (±100° C.), the decomposition of the inorganic carbon compounds in the sample of drill cuttings produces mainly $CO_2$ and starts later, at a set of instants in time around 125±25 seconds. The decomposition of the inorganic carbon compounds does not start at the beginning of the reaction. Chemically speaking, the inorganic carbon compounds are more thermally stable than the organic carbon compounds.

Figure 7:
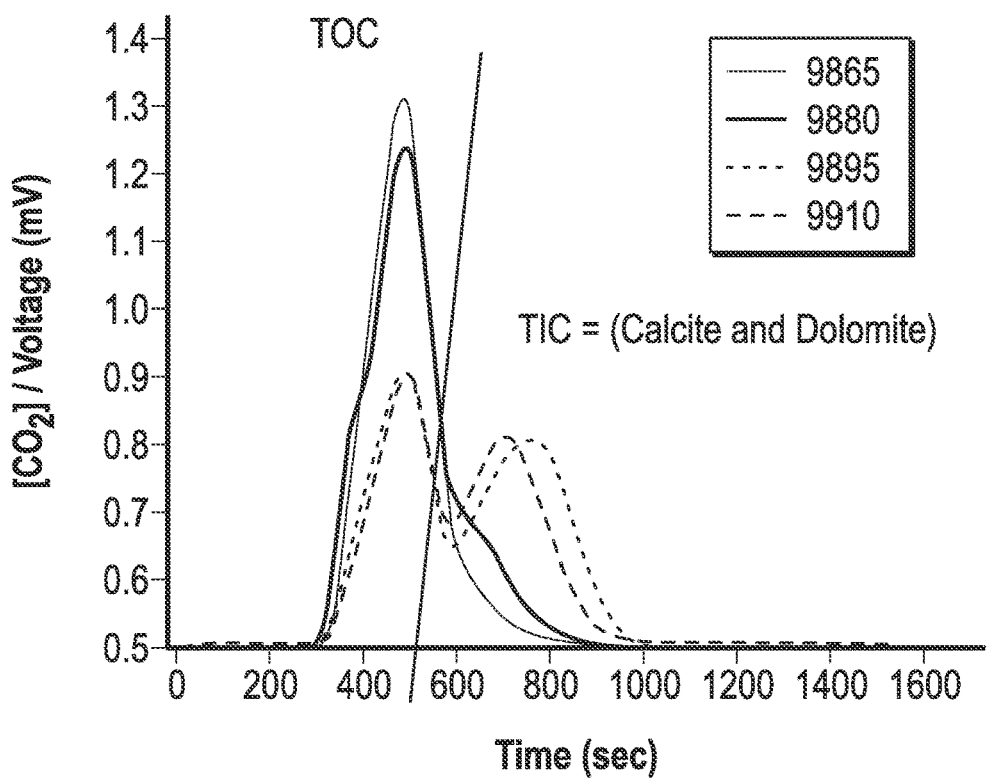
FIG. 7 is a graph showing an increase of TIC in a superposition of samples of drill cuttings from various well-bore depths of a carbonate formation analyzed by a high-temperature isothermal analysis according to some embodiments of the present disclosure where the total organic carbon (TOC) and the total inorganic carbon (TIC) are specified as a function of time.

Referring now to FIG. 7, in one embodiment where a sample of drill cuttings was obtained through drilling with water-based drilling mud, an organic carbon peak with a shoulder and a low inorganic carbon contribution were observed with the isothermal analysis system 110 according to the present disclosure. As will be appreciated by persons of ordinary skill in the art having the benefit of the instant disclosure, where a peak of total organic carbon includes two contributions for the TOC as illustrated in FIG. 7, the TOC present in the drill cuttings mainly include oil and kerogen. In this case, the set of instants in time where the maximum $CO_2$ is released is informative of the type of organic matter present in the sample of drill cuttings. The oil fraction is expected to appear earlier in time compared to the kerogen fraction. In some embodiments, the database system 132 may include data indicative of calibrated oil and kerogen peak times which can be used to recognize the oil fraction and the kerogen fraction.

Figure 8:
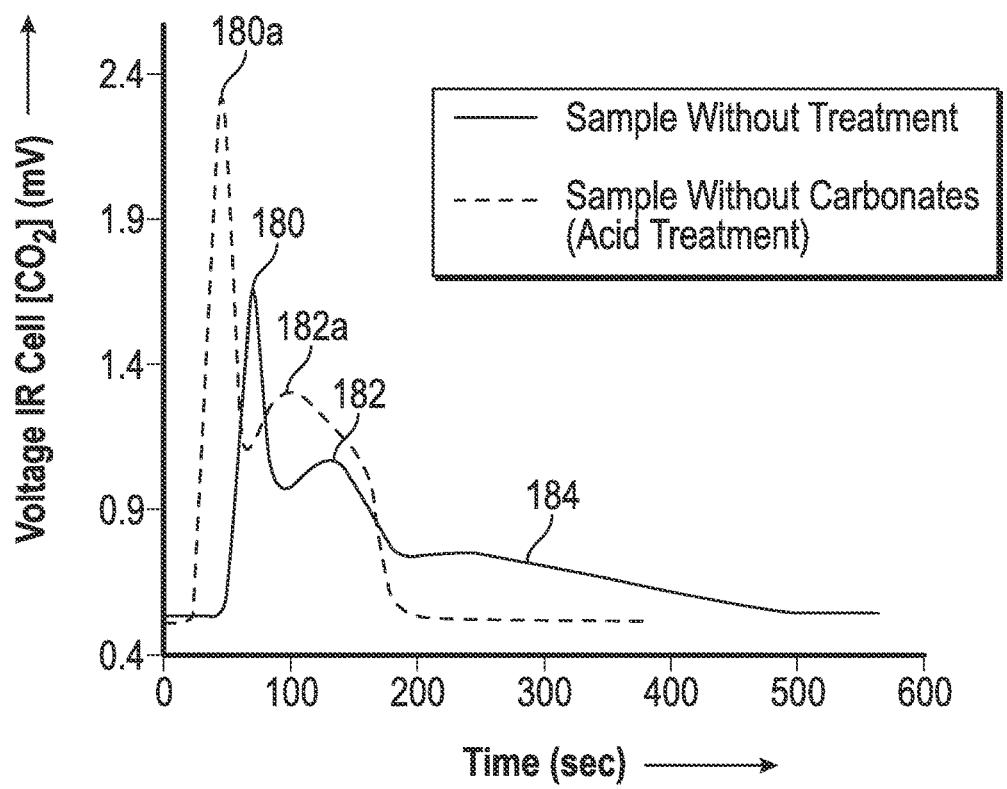
FIG. 8 is a graph showing an identification of an inorganic carbon peak by a high-temperature isothermal analysis method according to some embodiments of the present disclosure.

Referring now to FIG. 8, in one embodiment, a sample of drill cuttings contaminated by oil based mud was analyzed by the isothermal analysis system 110 according to the present disclosure and three peaks 180, 182, and 184, respectively, were observed and distinguished. As a control, a portion of the sample of drill cuttings was placed in a belcher with acid (hypochlorite acid, HCl) to allow the substantially complete reaction of the carbonates present in the sample of drill cuttings. Once the carbonates were reacted, the carbonate-free sample of drill cuttings was analyzed by the thermal analysis system 110 as described above. The results demonstrate that the third peak 184 is no longer observed, and two peaks 180*a* and 182*a* remain observed and distinguished, which indicated that the third peak 184 is indicative of the inorganic carbons present in the sample of drill cuttings.

Figure 9:
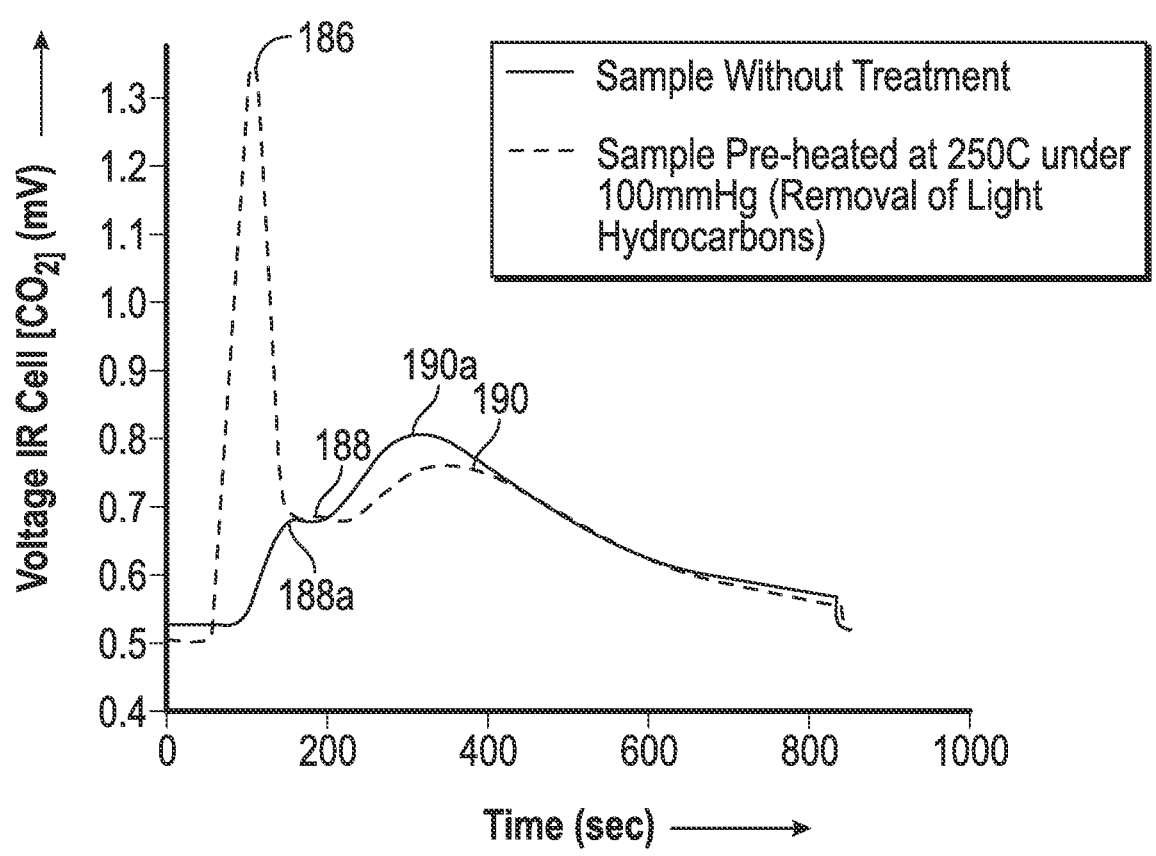
FIG. 9 is a graph showing an identification of light volatile molecules peak by a high-temperature isothermal analysis method according to some embodiments of the present disclosure where a high-temperature isothermal method is used.

Referring now to FIG. 9, in one embodiment a sample of drill cuttings contaminated by oil based mud was analyzed by the isothermal analysis system 110 via a high-temperature isothermal analysis according to embodiments of the present disclosure and three peaks 186, 188, and 190 were identified. As a control, a portion of the sample of drill cuttings was placed at 250° C. under 100 mmHg (low pressure, or less than atmospheric pressure) to remove the light carbon compounds present in the sample of drill cuttings. The decontaminated sample of drill cuttings was then analyzed by the instantaneous thermal analysis system 110 as described above, and the peaks 188*a* and 190*a* were observed, while the peak 186 was no longer observed. The results demonstrate that the first peak 186 is indicative of or can be attributed to light hydrocarbon present in the oil based drilling mud.

As will be appreciated by persons of ordinary skill in the art, data from samples with known amounts of the three types of carbons (i.e., light carbon compounds, organic carbons, and inorganic carbons) may be stored to build the information within the database system 132 that can be used as described herein to calculate the total amount of organic carbon compounds present in the sample of drill cuttings as well as the timing in which the presence of the three types of carbons can be detected in the data. The light molecules are associated to the contamination as soon as diesel, oil or synthetic polymers are used for the drilling process, otherwise it will be considered to come from the rock formation, consequently the detection and quantification of the light fraction is an advantage of both the high-temperature and the low-temperature embodiments of isothermal analysis methods described herein, whatever the temperature used (e.g., 650° C.±100° C. for the low-temperature isothermal analysis, or 1000° C.±100° C. for the high-temperature isothermal analysis).

Further, the mathematical analysis of the data may be optimized by other sources of information regarding the sample, such as mineralogical data, for example. In some embodiments, the amount of inorganic carbon (e.g., carbonates) may be determined using X-ray diffraction or spectroscopic analysis or else and stored in the database system 132, so that the value of carbon from organic matter determined via high-temperature isothermal analysis by the isothermal analysis system 110 becomes even more consistent by accurately factoring in the amount of inorganic carbon present in the sample.

An additional data using X-ray diffraction or else may be incorporated where samples of drill cuttings include siderite for the high-temperature isothermal analysis. Siderite reacts faster than calcite and dolomite; consequently siderite may interfere with the organic carbon peak. A systematic and mathematical correction may be implemented to the calculation of the total inorganic carbon and so to the total organic carbon for such drill cutting samples containing siderite.

In some embodiments, the analysis of the data from the detector 138 may be carried out by storing and accessing data indicative of waveforms in the nature of unique thermal fingerprints of multiple samples of drill cuttings stored in the database system 132, where multiple samples of drill cutting are analyzed in the same conditions and the corresponding data is stored in the database system 132. Samples of drill cuttings with known amounts of carbonates (Calcite, Dolomite), organic matter (Kerogen, Bitumen) and Diesel may be analyzed by the isothermal analysis system 110, and the set of instants in time corresponding to the maximum of each peak observed may be recorded, compared, and correlated with the respective carbon source, and the data may be stored in the database system 132. The database system 132 enables the isothermal analysis system 110 to accurately account for the potential partial overlap between adjacent peaks. Likewise, at the well-site, a typical drilling mud sample (e.g., water based mud or oil based mud) may be analyzed by the isothermal analysis system 110 and the corresponding data may be stored in the database system 132 to better adjust the mathematical processing of the accrual drill cuttings sample data by identifying a set of instants in time when a peak due to contaminants form the drilling mud is expected to be observed.

Figure 10:
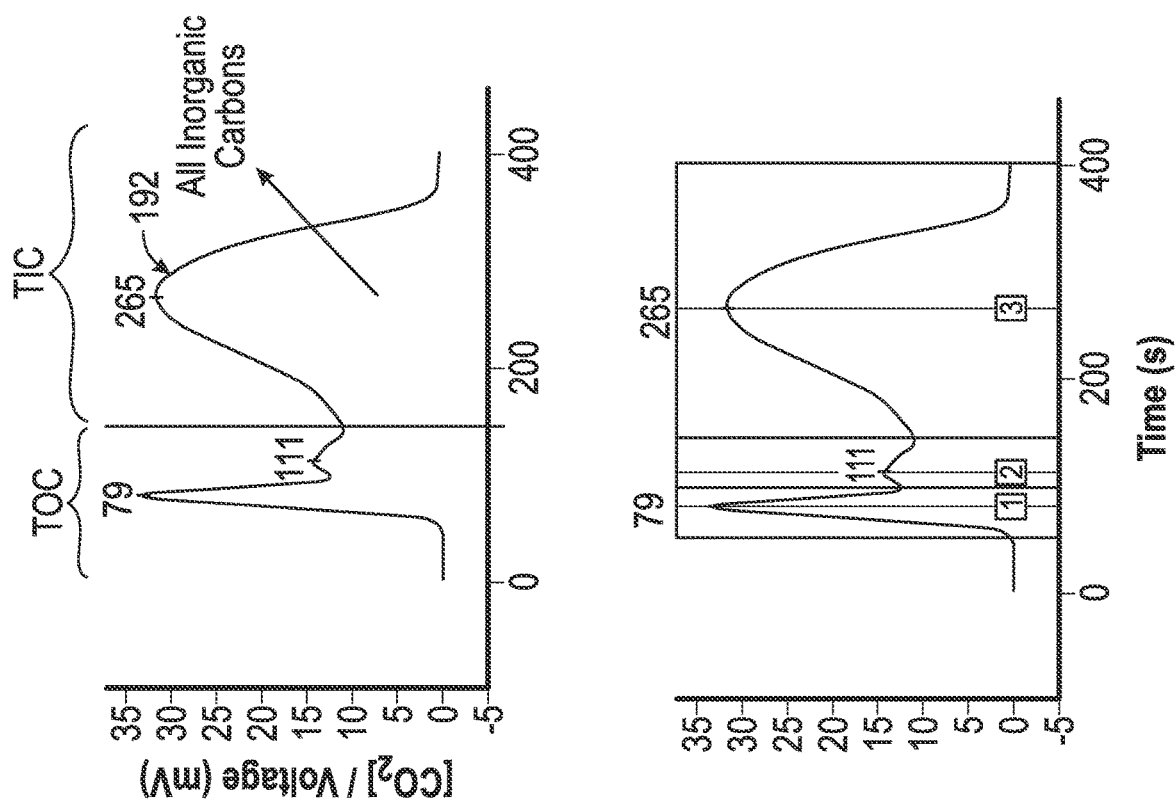
FIG. 10 is a graph showing the decomposition of calcite and dolomite for a high-temperature isothermal analysis method at 1000° C. (±100° C.) according to some embodiments of the present disclosure.
Figure 10:
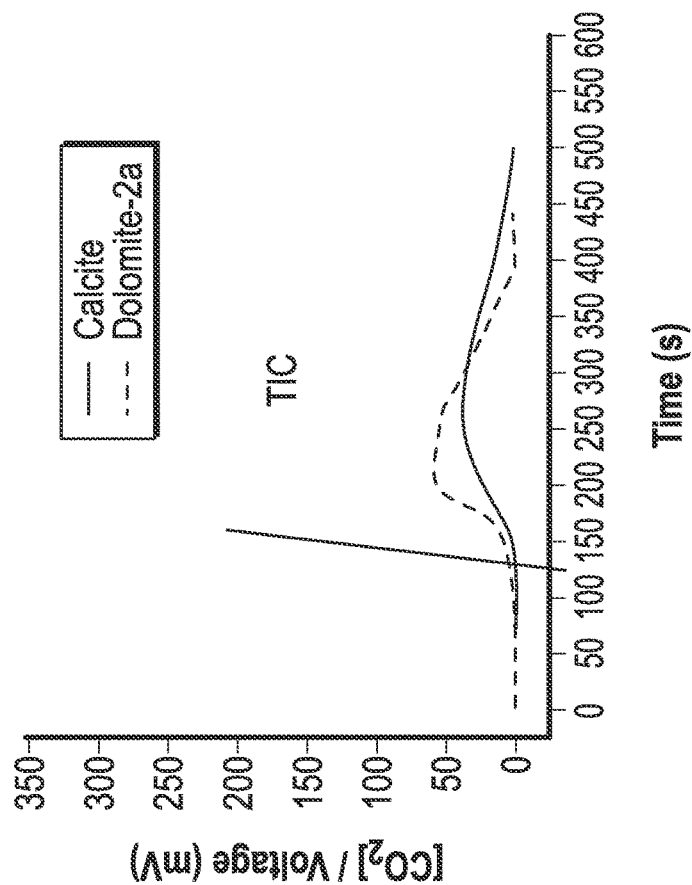

Referring now to FIG. 10, decomposition of calcite and dolomite at high temperature is shown therein via a high-temperature isothermal analysis. As the total surface area of the peaks is related to the carbons measured, surface area of the last peak 192 is the one related to the total inorganic carbons (TIC).

Knowing that:

Total carbons (TC)=Total organic carbons (TOC)+Total inorganic carbons (TIC), the total organic carbons can be determined by subtraction. TC is measured by the analyzer 114 via a calibration and TIC is deduced from the spectra, especially by calculating the surface area of the peak indicative of the organic carbon compounds present in the sample of drill cuttings.

Figure 11:
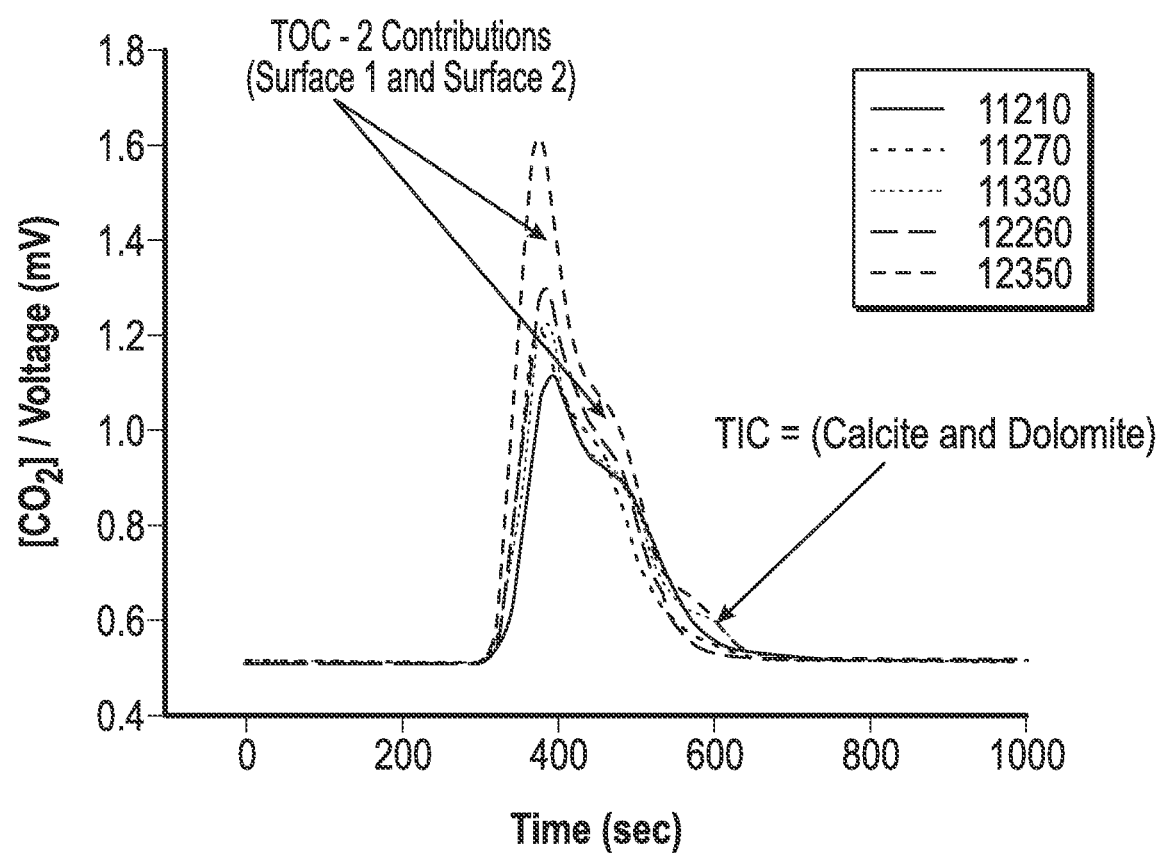
FIG. 11 is a graph showing superposition of samples of water-based drill cuttings analyzed by a high-temperature isothermal analysis method according to some embodiments of the present disclosure.

Referring now to FIG. 11, in some embodiments where the peak of the total organic carbon includes many contributions, very light molecules, oil and kerogen fractions are present in the drill cuttings. In this case, additional parameters can be calculated by the isothermal analysis system 110 according to the present disclosure, such as the ratio of the various contributions or the ratio of the oil fraction to the ratio of the kerogen fraction, for example. The total organic content in the sample of drill cuttings includes the waveform surface areas of the various contributions, which allows for any desired calculations to be carried out by the isothermal analysis system 110 to characterize and differentiate the organic matter and the various samples of drill cuttings.

In some embodiments where the drill cuttings have been drilled with oil-based drilling mud, the total organic matter in the drill cuttings includes oily contributions from the drilling mud that are expected to appear as a peak at the early stage of the analysis of a sample of the drill cuttings by the isothermal analysis system 110 according to the present disclosure. The earliest peak observed by the isothermal analysis system 110 is mainly due to the presence of the oil-based mud contamination in the drill cuttings, consequently the earliest peak may be subtracted from the calculation of the TOC to avoid an over-estimation. An advantage of using the isothermal analysis system 110 and methods according to the present disclosure is evaluating the influence of the contamination peak (e.g., the earliest peak), and avoiding cleaning the samples while the remained of the signal is useful to measure the TOC.

Figure 12:
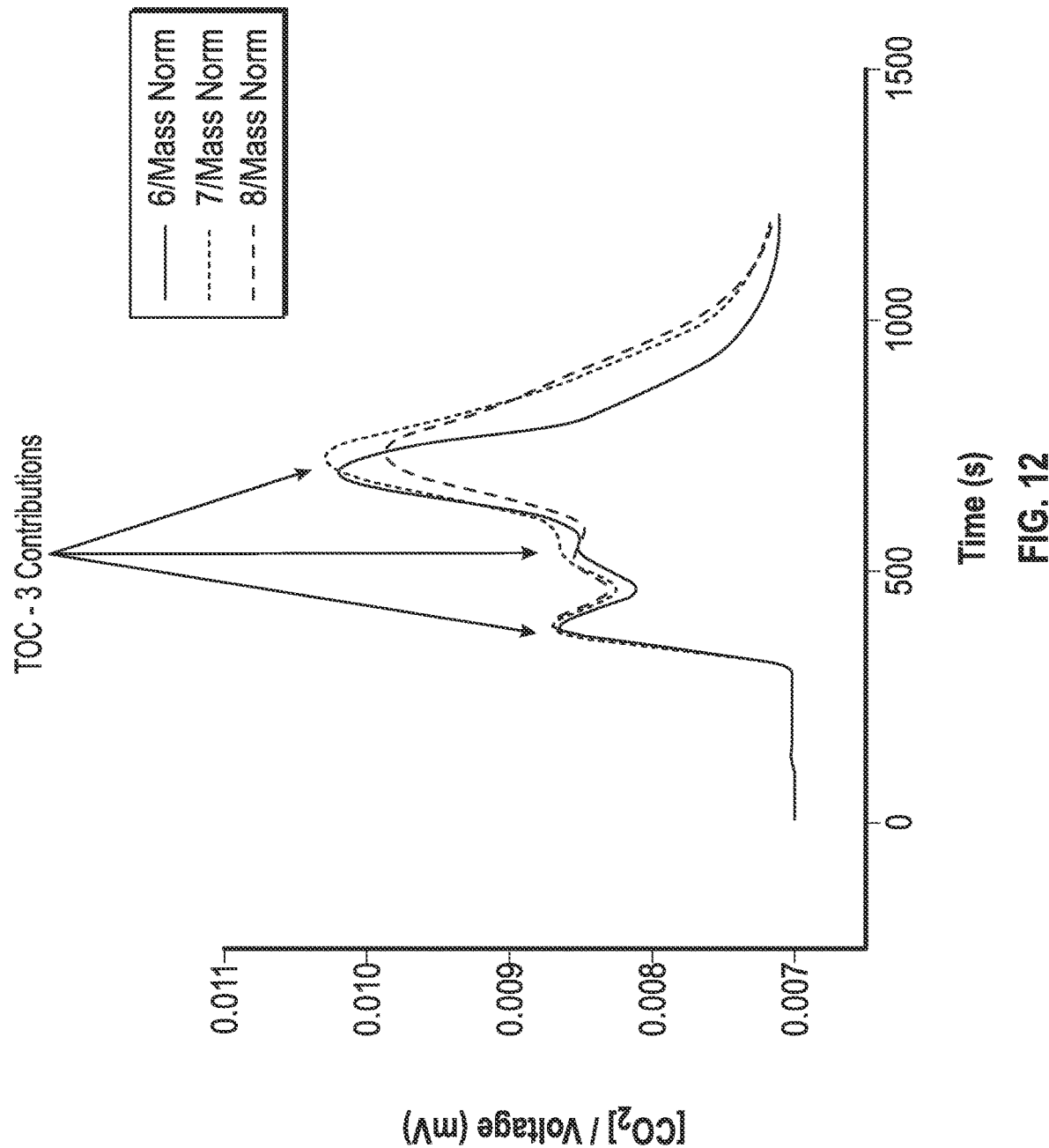
FIG. 12 is a graph showing the total organic carbon in drill cuttings analyzed by a low-temperature isothermal analysis at a constant temperature of about 650° C. (±100° C.) according to some embodiments of the present disclosure where only the organic carbon will react, and no carbonate contribution is observed.
Figure 13:
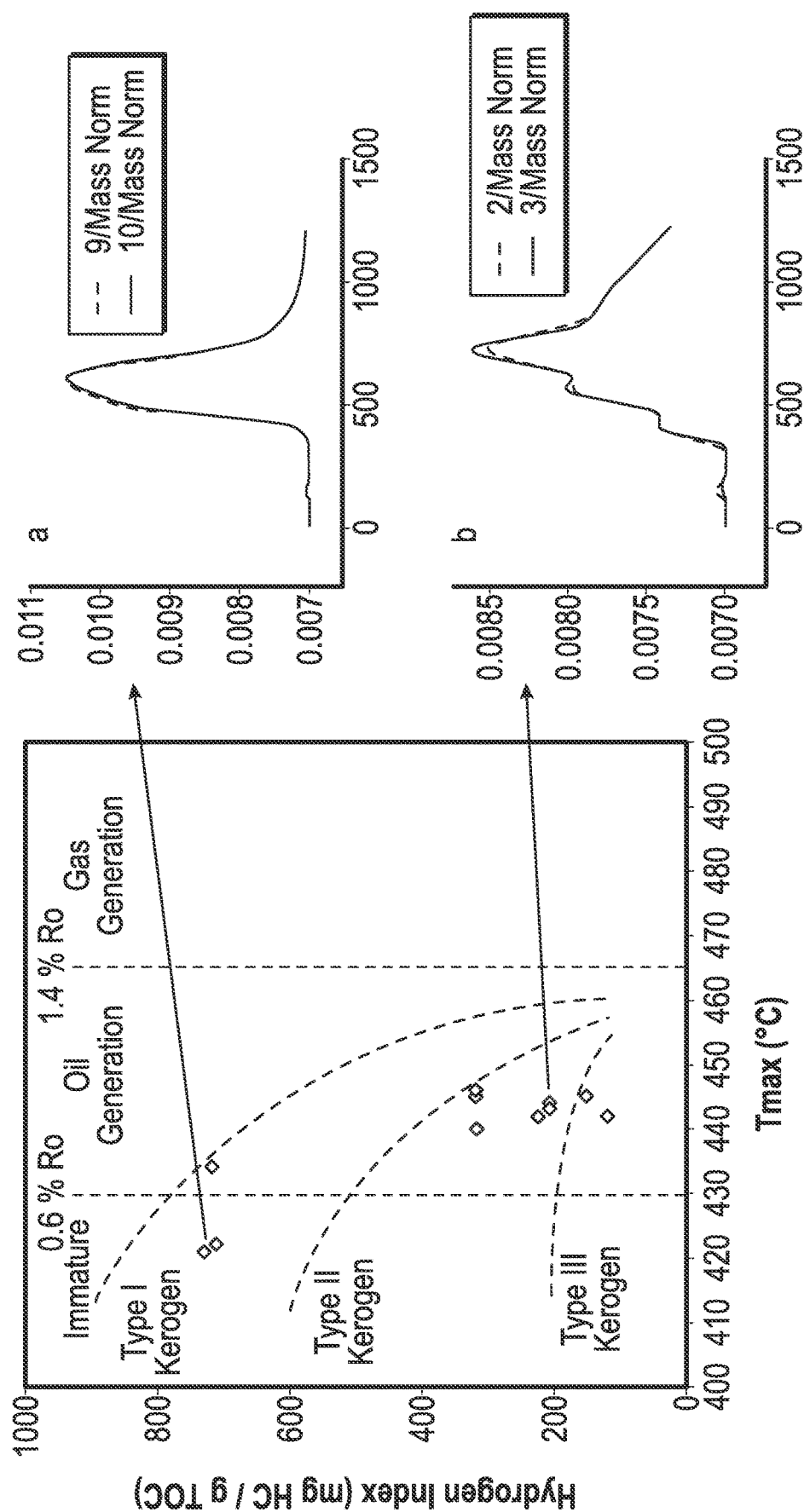
FIG. 13 is a graph showing a thermal fingerprint for organic carbon determined via a low-temperature isothermal analysis at a constant temperature of about 650° C. (±100° C.) according to some embodiments of the present disclosure.

Referring now to FIGS. 12-13, in one embodiment a low-temperature isothermal analysis was carried out by the isothermal analysis system 110 at a temperature of about 620° C. (relatively low temperature). A weighed sample of drill cuttings in the form of a powder sieved under 150 µm was rapidly introduced into the preheated furnace 136 at a substantially constant temperature of about 620° C., to cause an instantaneous thermal degradation of the organic carbons present in the sample, where the inorganic carbons will not react.

Under a constant flow of air the drill cuttings were combusted such that the organic carbons reacted into $CO_2$ and $H_2O$. In this case the shape of the curve is expected be related mainly to the organic carbons present in the sample of drill cuttings and to depend on the nature and particular composition of the organic carbons present in the sample of drill cuttings. In this case, the TOC may be directly calculated by the isothermal analysis system 110 because substantially no inorganic carbons react at this temperature relatively low temperature (e.g., TIC=0).

Referring now to FIG. 12, in one embodiment drill cuttings were drilled using a water-based mud. In this case, the total signal provided to the processor 116 by the detector 138 was linked to the organic carbons present in the drill cuttings. The shape of the curve and the various contributions are attributed to various particular organic carbons (e.g., by number of carbon atoms in the carbon compound), meaning that various calculations can be done to differentiate source rocks, such as the calculation done by Rock-Eval 6, for example, or any other desired calculations as will be appreciated by persons of ordinary skill in the art having the benefit of the instant disclosure.

As shown in FIG. 13, in one embodiment where samples of two types of drill cuttings are analyzed in parallel by conventional geochemistry methods such as Rock-Eval 6, the type of kerogen present in the sample of drill cuttings can be highlighted and the measurement proposed meaning the isothermal reaction at 620° C. For example, kerogen type I (immature) may be identified by $CO_2$ produced at one peak during an isothermal reaction, and kerogen II (oil window) may be identified by $CO_2$ produced at four peaks during an isothermal reaction as described herein.

To conclude, the isothermal analysis system 110, and methods described herein may be used to analyze contaminated drill cuttings. The drill cuttings may be ground prior to introduction into the furnace 136. For the contaminated samples of drill cuttings or other solids, such as drill cuttings obtained through drilling with oil base mud or synthetic polymer, the identification of each contribution of carbon by time and the associated mathematical program allows at least the amount of TOC present in the sample of drill cuttings to be directly calculated according to the present disclosure.

Although the preceding description has been described herein with reference to particular means, materials and embodiments, it is not intended to be limited to the particulars disclosed herein; rather, it extends to all functionally equivalent structures, methods and uses, such as are within the scope of the appended claims.

The present disclosure relates in particular to any computer system comprising an input port, an output port, and at least one processor coupled with the input and output ports and executing processor-executable code stored in a non-transitory processor-readable medium, the processor-executable code causing the at least one processor to:
  receive a signal via the input port, the signal including data indicative of the amount of said combustion products as a function of time;
  process the data with a predetermined logic according to the substantially constant temperature to:
    locate at least one peak in the amount of the at least one combustion product, the at least one peak produced by the sample of drill cuttings at a set of instants in time;
    correlate the set of instants in time with the presence of at least one of organic carbon compounds from at least one contaminant present in the sample of drill cuttings, organic carbon compounds present in the sample of drill cuttings, and inorganic carbon compounds present in the sample of drill cuttings; and
    calculate at least one of an amount of contaminant present in the sample of drill cuttings, a total amount of organic carbon compounds present in the sample of drill cuttings, and a total amount of inorganic carbon compounds present in the sample of drill cuttings, at least partially based on the at least one peak; and
  output at least one signal indicative of at least one of the amount of contaminant present in the sample of drill cuttings, the total amount of organic carbon compounds present in the sample of drill cuttings, and the total amount of inorganic carbon compounds present in the sample of drill cuttings via the output port.

Such a computer system may comprise any combination of the following features:
  the at least one peak is a first peak and the set of instants in time is a first set of instants in time, and the processor-executable code further causes the at least one processor to:
    locate at least one second peak in the amount of the at least one combustion product, the second peak produced by the sample of drill cuttings at a second set of instants in time later than the first set of instants in time;
    correlate the first set of instants in time with a first organic carbon compound present in the sample of drill cuttings, and the second set of instants in time with a second organic carbon compound present in the sample of drill cuttings, the second organic carbon compound being different from the first organic carbon compound; and
  calculate an amount of the first organic carbon compound and an amount of the second organic carbon compound present in the sample of drill cuttings at least partially based on the first and second peaks.
    the processor-executable code causes the at least one processor to calculate a ratio of the amount of the first organic carbon to the amount of second organic carbon compound present in the sample of drill cuttings;
    the set of instants in time is a first set of instants in time, and wherein the at least one processor correlates the first set of instants in time with the presence of at least one of the organic carbon compounds from at least contaminant present in the sample of drill cuttings, the organic carbon compounds present in the sample of drill cuttings and the inorganic carbon compounds present in the sample of drill cuttings by accessing data stored in a non-transitory processor-readable medium, the data also indicative of a second set of instants in time correlated with the presence of at least one of the organic carbon compounds from at least contaminant present in the sample of drill cuttings, the organic carbon compounds present in the sample of drill cuttings and the inorganic carbon compounds present in the sample of drill cuttings. In particular, the at least one processor correlates the first set of instants in time with the presence of at least one of the organic carbon compounds from at least contaminant present in the sample of drill cuttings and the inorganic carbon compounds present in the sample of drill cuttings by accessing data stored in a non-transitory processor-readable medium, the data also indicative of a second set of instants in time correlated with the presence of the organic carbon compounds present in the sample of drill cuttings.
  the second set of instants in time at least partially overlaps with the first set of instants in time,
  the peak is a first peak and the set of instants in time is a first set of instants in time, and the processor-executable code causes the at least one processor to process the data according to the predetermined logic to correlate the first peak with organic carbon compounds present in the sample of drill cuttings, respectively organic carbon compounds present in at least one contaminant in the sample of drill cuttings, and wherein the processor-executable code further causes the at least one processor to locate a second peak produced by the sample of drill cuttings at a second set of instants in time and correlate the second peak with the presence of inorganic carbon compounds in the sample of drill cuttings, respectively organic carbon compounds in the sample of drill cuttings, the second set of instants in time being later than the first set of instants in time,
  the at least one peak is a first peak and the set of instants in time is a first set of instants in time, and the processor-executable code further causes the at least one processor to:
    locate at least one second peak in the amount of the at least one combustion product, the second peak produced by the sample of drill cuttings at a second set of instants in time later than the first set of instants in time;
    correlate the first set of instants in time with organic carbon compounds from a contaminant present in the sample of drill cuttings, and the second set of instants in time with organic carbon compounds present in the sample of drill cuttings; and
    calculate a total amount of organic carbon compounds present in the sample of drill cuttings, at least partially based on the first and second peaks.
  the at least one processor is configured so that at least one of the an amount of contaminant present in the sample of drill cuttings, the total amount of organic carbon compounds present in the sample of drill cuttings, and the total amount of inorganic carbon compounds present in the sample of drill cuttings is calculated directly and only based on the located peaks;

The present disclosure also relates in particular to any isothermal analysis system comprising any embodiment of a computer system as disclosed above and any analyzer including:

a furnace having a sample chamber for receiving a sample of drill cuttings obtained from a well-bore;

a controller coupled with the furnace so as to maintain substantially constant temperature inside the furnace, a detector for detecting the amount of at least one combustion product produced by the sample subjected to an oxidation reaction in the furnace, Such system may comprise any combination of the following features:

the detector is an infrared detector guaranteeing a simple and quick detection. It may however be any other type of detector;

the detector is configured to detect at least one of the following combustion product: carbon monoxide (CO) or dioxide ($CO_2$), the detector is configured to detect one or several of the following combustion product: carbon monoxide (CO), carbon dioxide ($CO_2$), sulfur dioxide ($SO_2$), nitrogen oxide (NO), nitrogen dioxide ($NO_2$) or water ($H_2O$), the constant temperature is between 900° C. and 1100° C., in particular about 1000° C., the constant temperature is between 550° C. and 750° C., in particular about 650° C., at least the analyzer is situated at the well-site. The computer system may be located at the well-site or remotely.

The present disclosure also relates to any isothermal analysis method comprising:

heating a sample chamber of a furnace to a temperature regulated to a substantially constant temperature, optionally within a range of 500° C. to 1100° C.;

placing a sample of drill cuttings obtained from a well-bore into the sample chamber detecting the amount of at least one combustion product produced by the sample subjected to the oxidation reaction inside of the furnace;

transmitting a signal to an input port of at least one processor executing processor-executable code stored in a non-transitory processor readable medium, the signal including data indicative of an amount of said combustion products as a function of time;

processing the data by the at least one processor with a predetermined logic stored in a non-transitory processor-readable medium to locate at least one peak in the amount of the at least one combustion product produced by the sample of drill cuttings and calculate a total amount of organic carbon present in the sample of drill cuttings; and outputting, by the at least one processor via an output port, at least one signal indicative of the total amount of organic carbon compounds present in the sample of drill cuttings.

Such method may be performed with any analysis system described above, and may further comprise any combination of the following features:

preparing the sample obtained from the wellbore before heating it, consisting in one or several of the following:
        drying the cuttings of the sample,
        grinding the cuttings of the sample,
        sieving the cuttings of the sample, and
        weighing the sample.

extracting drill cuttings from the wellbore, outputting the signal being performed less than 1 hour, in particular less than 30 minutes after the extraction of the cuttings.

The disclosure also relates to a sample preparation method for preparing drill cuttings extracted from a wellbore to an analysis method, consisting in one or several of the following:

drying the cuttings of the sample,
    grinding the cuttings of the sample,
    sieving the cuttings of the sample, and
    weighing the sample.

Such a method does not include any other steps as the ones disclosed above and enable a simple preparation of the samples, such a preparation being sufficient for performing the analysis.

What is claimed is:

1. An isothermal analysis system comprising:

an analyzer including:

an oxidation furnace having a sample chamber for receiving a sample of drill cuttings obtained from a well-bore and for subjecting the sample to an oxidation reaction;

a controller coupled with the oxidation furnace and operated to maintain a substantially constant temperature above 550° C. inside the furnace;

a detector for detecting the amount of at least one combustion product produced by the sample subjected to the oxidation reaction, wherein the at least one combustion product comprises at least one of carbon monoxide (CO) or dioxide (CO2);

a computer system comprising an input port, an output port, and at least one processor coupled with the input and output ports and executing processor-executable code stored in a non-transitory processor-readable medium, the processor-executable code causing the at least one processor to:

receive a signal via the input port, the signal including data indicative of the amount of said combustion products as a function of time;

process the data with a predetermined logic according to the substantially constant temperature to:

locate a first peak in the amount of the at least one combustion product, wherein the first peak is produced by the sample of drill cuttings at a first set of instants in time, and wherein the first peak is indicative of at least one contaminant present in the sample, and wherein the at least one contaminant comprises volatile organic compounds associated with oil-based mud present in the sample of drill cuttings;

locate a second peak in the amount of the at least one combustion product, wherein the second peak produced by the sample of drill cuttings at a set of instants in time, wherein the second set of instants in time occurs subsequent to the first set of instants in time;

correlate the second set of instants in time with the presence of at least one of organic carbon compounds present in the sample of drill cuttings, and inorganic carbon compounds present in the sample of drill cuttings; and calculate at least one of a total amount of organic carbon compounds present in the sample of drill cuttings, and a total amount of inorganic carbon compounds present in the sample of drill cuttings, at least partially based on the second peak; and output at least one signal indicative of at least one of the amount of contaminant present in the sample of drill cuttings, the total amount of organic carbon compounds present in the sample of drill cuttings, and the total amount of inorganic carbon compounds present in the sample of drill cuttings via the output port.

2. The analysis system of claim 1, wherein the detector is an infrared detector.

3. The analysis system of claim 1, wherein the detector is configured to detect one or several of the following combustion product: carbon monoxide (CO), carbon dioxide ($CO_2$), sulfur dioxide ($SO_2$), nitrogen oxide (NO), nitrogen dioxide ($NO_2$) or water ($H_2O$).

4. The analysis system according to claim 1, wherein the constant temperature is between 900° C. and 1100° C., in particular about 1000° C.

5. The analysis system according to claim 1, wherein the constant temperature is between 550° C. and 750° C., in particular about 650° C.

6. The analysis system of claim 1, and wherein the processor-executable code further causes the at least one processor to:
locate a third peak in the amount of the at least one combustion product, the second peak produced by the sample of drill cuttings at a third set of instants in time, wherein the third set of instants in time occurs subsequent to the second set of instants in time;
correlate in time with a first organic carbon compound present in the sample of drill cuttings the second set of instants, and the second set of instants in time with a second organic carbon compound present in the sample of drill cuttings, the second organic carbon compound being different from the first organic carbon compound; and
calculate an amount of the first organic carbon compound and an amount of the second organic carbon compound present in the sample of drill cuttings at least partially based on the second and third peaks.

7. The analysis system of claim 6, wherein the processor-executable code further causes the at least one processor to calculate a ratio of the amount of the first organic carbon to the amount of second organic carbon compound present in the sample of drill cuttings.

8. The analysis system according to claim 1, wherein the at least one processor correlates the first set of instants in time with the presence of at least one of the the at least one contaminant present in the sample of drill cuttings by accessing data stored in a non-transitory processor-readable medium, the data also indicative of a second set of instants in time correlated with the presence of at least one of the organic carbon compounds from the at least one contaminant present in the sample of drill cuttings, the organic carbon compounds present in the sample of drill cuttings and the inorganic carbon compounds present in the sample of drill cuttings.

9. The analysis system of claim 1, wherein the at least one processor correlates the second set of instants in time with the presence of at least one of the organic carbon compounds from the at least one contaminant present in the sample of drill cuttings and the inorganic carbon compounds present in the sample of drill cuttings by accessing data stored in a non-transitory processor-readable medium, the data also indicative of a second set of instants in time correlated with the presence of the organic carbon compounds present in the sample of drill cuttings.

10. The analysis system of claim 1, wherein the second set of instants in time at least partially overlaps with the first set of instants in time.

11. The analysis system according to claim 1, wherein the peak is a first peak and the set of instants in time is a first set of instants in time, and wherein the processor-executable code further causes the at least one processor to process the data according to the predetermined logic to correlate the first peak with the organic carbon compounds present in the sample of drill cuttings, and wherein the processor-executable code further causes the at least one processor to locate a second peak produced by the sample of drill cuttings at a second set of instants in time and correlate the second peak with the presence of the inorganic carbon compounds in the sample of drill cuttings, the second set of instants in time being later than the first set of instants in time.

12. The analysis system according to claim 1, wherein the at least one processor is configured so that at least one of the amount of contaminant present in the sample of drill cuttings, the total amount of organic carbon compounds present in the sample of drill cuttings, and the total amount of inorganic carbon compounds present in the sample of drill cuttings is calculated directly and only based on the located peaks.

13. The analysis system according to claim 1, wherein at least the analyzer is situated at the well-site.

14. The analysis system of claim 1, wherein the sample chamber contains an oxidizing atmosphere.

15. The analysis system of claim 1, configured so that the sample chamber is subjected to a constant flow of air.

16. The analysis system of claim 1, wherein the volatile organic compounds comprise hydrocarbons.

17. An isothermal analysis method, comprising:
heating a sample chamber of an oxidation furnace to a temperature regulated to a substantially constant temperature above 550° C.;
placing a sample of drill cuttings obtained from a wellbore into the sample chamber and subjecting the sample to an oxidation reaction inside of the oxidation furnace;
detecting the amount of at least one combustion product produced by the sample subjected to the oxidation reaction, wherein the at least one combustion product comprises at least one of carbon monoxide (CO) or dioxide ($CO_2$);
transmitting a signal to an input port of at least one processor executing processor-executable code stored in a non-transitory processor readable medium, the signal including data indicative of an amount of said combustion products as a function of time;
processing the data by the at least one processor with a predetermined logic stored in a non-transitory processor-readable medium to:
locate a first peak produced by the sample of drill cuttings at a first set of instants in time, wherein the first peak is indicative of at least one contaminant present in the sample, and wherein the at least one contaminant comprises volatile organic compounds associated with oil-based mud present in the sample of drill cuttings;
locate a second peak in the amount of the at least one combustion product produced by the sample of drill cuttings at a second set of instants in time based on locating the first peak, wherein the second set of instants in time occurs subsequent to the first set of instants in time;
calculate a total amount of organic carbon present in the sample of drill cuttings based on the second peak; and outputting, by the at least one processor via an output port, at least one signal indicative of the total amount of organic carbon compounds present in the sample of drill cuttings.

18. The method of claim 17, also comprising a preparing the sample obtained from the wellbore before heating it, consisting in one or several of the following:

drying the cuttings of the sample,
grinding the cuttings of the sample,
sieving the cuttings of the sample, and
weighing the sample.

19. The method of claim 17, comprising extracting drill cuttings from the wellbore, outputting the signal being performed less than 1 hour, in particular less than 30 minutes, after the extraction of the cuttings.

20. The method of claim 17, wherein the constant temperature of the oxidation reaction is within a range of 500° C. to 1100° C.

21. The method of claim 17, wherein the volatile organic compounds comprise hydrocarbons.

* * * * *